(12) United States Patent
Leonhardt

(10) Patent No.: US 11,602,627 B2
(45) Date of Patent: Mar. 14, 2023

(54) CIRCULATORY ASSIST PUMP

(71) Applicant: Second Heart Assist, Inc., Salt Lake City, UT (US)

(72) Inventor: Howard J. Leonhardt, Corona Del Mar, CA (US)

(73) Assignee: Second Heart Assist, Inc., Salt Lake City, UT (US)

( * ) Notice: Subject to any disclaimer, the term of this patent is extended or adjusted under 35 U.S.C. 154(b) by 0 days.

(21) Appl. No.: 16/982,908

(22) PCT Filed: Mar. 20, 2019

(86) PCT No.: PCT/US2019/023208
§ 371 (c)(1),
(2) Date: Sep. 21, 2020

(87) PCT Pub. No.: WO2019/183247
PCT Pub. Date: Sep. 26, 2019

(65) Prior Publication Data
US 2021/0008263 A1    Jan. 14, 2021

Related U.S. Application Data

(60) Provisional application No. 62/694,564, filed on Jul. 6, 2018, provisional application No. 62/682,046, filed
(Continued)

(51) Int. Cl.
*A61M 60/139* (2021.01)
*A61M 60/148* (2021.01)
(Continued)

(52) U.S. Cl.
CPC .......... *A61M 60/148* (2021.01); *A61M 60/13* (2021.01); *A61M 60/139* (2021.01);
(Continued)

(58) Field of Classification Search
CPC .............. A61M 60/135; A61M 60/148; A61M 60/139; A61M 60/216
See application file for complete search history.

(56) References Cited

U.S. PATENT DOCUMENTS

| | | | |
|---|---|---|---|
| 3,620,212 A | 11/1971 | Fannon et al. | |
| 3,786,806 A | 1/1974 | Johnson et al. | |
| (Continued) | | | |

FOREIGN PATENT DOCUMENTS

| | | |
|---|---|---|
| AU | 2001275476 A1 | 12/2001 |
| AU | 2014296320 B2 | 2/2015 |
| (Continued) | | |

OTHER PUBLICATIONS

An et al. "Novel electro-active shape memory polymers for soft actuators" 2020 The Japan Society of Applied Physics, Published May 13, 2020. vol. 59, No. 6.
(Continued)

*Primary Examiner* — Michael J D'Abreu
(74) *Attorney, Agent, or Firm* — TraskBritt

(57) ABSTRACT

A minimally invasive circulatory support platform that utilizes an aortic stent pump or pumps. The platform uses a low profile catheter-based techniques and provides temporary and chronic circulatory support depending on the needs of the patient. Also described is a catheter-based temporary assist pump to treat patients with acute decompensated heart failure and provide circulatory support to subjects undergoing high risk percutaneous coronary intervention ("PCI"). Further described is a wirelessly powered circulatory assist pump for providing chronic circulatory support for heart failure patients. The platform and system are relatively easy to place, have higher flow rates than existing systems, and provide improvements in the patient's renal function.

20 Claims, 8 Drawing Sheets

Related U.S. Application Data on Jun. 7, 2018, provisional application No. 62/645,599, filed on Mar. 20, 2018.

(51) Int. Cl.
*A61M 60/414* (2021.01)
*A61M 60/13* (2021.01)
*A61M 60/216* (2021.01)
*A61M 60/818* (2021.01)
*A61M 60/808* (2021.01)
*A61M 60/873* (2021.01)
*A61M 60/562* (2021.01)

(52) U.S. Cl.
CPC ........ *A61M 60/216* (2021.01); *A61M 60/414* (2021.01); *A61M 60/562* (2021.01); *A61M 60/808* (2021.01); *A61M 60/818* (2021.01); *A61M 60/873* (2021.01); *A61M 2205/3365* (2013.01); *A61M 2205/3523* (2013.01); *A61M 2205/8262* (2013.01)

(56) References Cited

U.S. PATENT DOCUMENTS

| | | |
|---|---|---|
| 3,890,977 A | 6/1975 | Wilson |
| 4,283,233 A | 8/1981 | Goldstein et al. |
| 4,580,568 A | 4/1986 | Gianturco |
| 4,753,221 A | 6/1988 | Kensey et al. |
| 4,925,443 A | 5/1990 | Heilman et al. |
| 5,092,878 A * | 3/1992 | Miyata ............... A61M 60/40 623/3.18 |
| 5,354,308 A | 10/1994 | Simon et al. |
| 5,507,303 A | 4/1996 | Kuzma |
| 5,507,662 A | 4/1996 | Nyman |
| 5,715,837 A | 2/1998 | Chen |
| 5,733,313 A | 3/1998 | Barreras et al. |
| 5,749,855 A | 5/1998 | Reitan |
| 5,782,907 A * | 7/1998 | Frantzen ............... A61F 2/88 623/1.13 |
| 5,895,416 A | 4/1999 | Barreras et al. |
| 5,957,949 A | 9/1999 | Leonhardt et al. |
| 5,964,771 A | 10/1999 | Beyar et al. |
| 6,166,518 A | 12/2000 | Echarri et al. |
| 6,185,452 B1 | 2/2001 | Schulman et al. |
| 6,315,721 B2 | 11/2001 | Schulman et al. |
| 6,390,969 B1 | 5/2002 | Bolling et al. |
| 6,472,991 B1 | 10/2002 | Schulman et al. |
| 6,690,970 B1 | 2/2004 | Taheri et al. |
| 6,738,672 B2 | 5/2004 | Schulman et al. |
| 6,821,154 B1 | 11/2004 | Canfield et al. |
| 6,839,596 B2 | 1/2005 | Nelson et al. |
| 6,889,087 B2 | 5/2005 | Moore |
| 6,947,782 B2 | 9/2005 | Schulman et al. |
| 7,005,935 B2 | 2/2006 | Moore |
| 7,015,769 B2 | 3/2006 | Schulman et al. |
| 7,024,249 B2 | 4/2006 | Weisner et al. |
| 7,108,711 B2 | 9/2006 | Vogel et al. |
| 7,114,502 B2 | 10/2006 | Schulman et al. |
| 7,157,150 B2 | 1/2007 | Jiang |
| 7,163,385 B2 | 1/2007 | Gharib et al. |
| 7,177,690 B2 | 2/2007 | Woods et al. |
| 7,225,032 B2 | 5/2007 | Schmeling et al. |
| 7,228,624 B2 | 6/2007 | Culp |
| 7,235,050 B2 | 6/2007 | Schulman et al. |
| 7,239,921 B2 | 7/2007 | Canfield et al. |
| 7,245,972 B2 | 7/2007 | Davis |
| 7,286,883 B2 | 10/2007 | Schulman et al. |
| 7,343,204 B2 | 3/2008 | Schulman et al. |
| 7,379,774 B2 | 5/2008 | Gord et al. |
| 7,437,193 B2 | 10/2008 | Parramon et al. |
| 7,450,998 B2 | 11/2008 | Zilberman et al. |
| 7,460,911 B2 | 12/2008 | Cosendai et al. |
| 7,513,257 B2 | 4/2009 | Schulman et al. |
| 7,542,804 B2 | 6/2009 | Mandell |
| 7,563,279 B2 | 7/2009 | Lasater |
| 7,599,743 B2 | 10/2009 | Hassler, Jr. et al. |
| 7,670,363 B2 | 3/2010 | Vogel et al. |
| 7,775,444 B2 | 8/2010 | Derocco et al. |
| 7,805,200 B2 | 9/2010 | Kast et al. |
| 7,841,976 B2 | 11/2010 | McBride et al. |
| 7,857,766 B2 | 12/2010 | Lasater et al. |
| 7,860,476 B1 | 12/2010 | Karr et al. |
| 7,883,325 B2 | 2/2011 | Kheradvar et al. |
| 7,945,334 B2 | 5/2011 | Jimenez et al. |
| 7,970,477 B2 | 6/2011 | Loeb et al. |
| 7,979,140 B2 | 7/2011 | Schulman |
| 7,993,259 B2 | 8/2011 | Kang et al. |
| 7,998,190 B2 | 8/2011 | Gharib et al. |
| 8,000,803 B2 | 8/2011 | Araujo |
| RE42,682 E | 9/2011 | Barreras, Sr. et al. |
| 8,012,079 B2 | 9/2011 | Delgado, III |
| 8,050,297 B2 | 11/2011 | Delmain et al. |
| 8,092,365 B2 | 1/2012 | Rinderknecht et al. |
| 8,099,647 B1 | 1/2012 | Karr et al. |
| 8,197,234 B2 | 6/2012 | Gharib et al. |
| 8,200,335 B2 | 6/2012 | Donofrio et al. |
| 8,277,404 B2 | 10/2012 | Einarsson |
| 8,361,165 B2 | 1/2013 | Karr et al. |
| 8,395,300 B2 | 3/2013 | Aabloo et al. |
| 8,447,402 B1 | 5/2013 | Jiang et al. |
| 8,545,255 B2 | 10/2013 | Litzler et al. |
| 8,555,894 B2 | 10/2013 | Schulman et al. |
| 8,579,789 B1 * | 11/2013 | Zilbershlag ......... A61M 60/148 607/34 |
| 8,579,858 B2 | 11/2013 | Reitan et al. |
| 8,585,571 B2 | 11/2013 | Bachman et al. |
| 8,617,239 B2 | 12/2013 | Reitan |
| 8,727,959 B2 | 5/2014 | Reitan et al. |
| 8,764,621 B2 | 7/2014 | Badstibner et al. |
| 8,781,589 B1 | 7/2014 | Jiang et al. |
| 8,849,398 B2 | 9/2014 | Evans |
| 8,956,275 B2 | 2/2015 | Bolyard et al. |
| 9,125,655 B2 | 9/2015 | Gharib et al. |
| 9,155,901 B2 | 10/2015 | Dearden et al. |
| 9,205,273 B2 | 12/2015 | Dearden et al. |
| 9,239,951 B2 | 1/2016 | Hoffberg et al. |
| 9,276,348 B1 | 3/2016 | Vadlamudi et al. |
| 9,277,366 B2 | 3/2016 | Busch |
| 9,308,303 B2 | 4/2016 | Badstibner et al. |
| 9,308,378 B2 | 4/2016 | Shelton et al. |
| 9,482,255 B2 | 11/2016 | Changsrivong et al. |
| 9,570,842 B2 | 2/2017 | Nordgren et al. |
| 9,572,915 B2 | 2/2017 | Heuring et al. |
| 9,608,537 B1 | 3/2017 | Lee |
| 9,616,159 B2 | 4/2017 | Anderson et al. |
| 9,622,677 B1 | 4/2017 | Stover et al. |
| 9,623,220 B2 | 4/2017 | Perrin et al. |
| 9,642,958 B2 | 5/2017 | Zilbershlag et al. |
| 9,656,009 B2 | 5/2017 | Gharib et al. |
| 9,675,807 B2 | 6/2017 | Schmidt |
| 9,724,523 B2 | 8/2017 | Calderon et al. |
| 9,750,428 B2 | 9/2017 | Matei et al. |
| 9,782,600 B2 | 10/2017 | Mazanec |
| 9,789,325 B2 | 10/2017 | Shelton et al. |
| 9,827,419 B2 | 11/2017 | Boggs, II et al. |
| 9,837,831 B2 | 12/2017 | Lee |
| 9,855,376 B2 | 1/2018 | Bluvshtein et al. |
| 9,855,436 B2 | 1/2018 | Dearden et al. |
| 9,876,308 B2 | 1/2018 | Jones et al. |
| D811,588 S | 2/2018 | Kaiser et al. |
| 9,889,242 B2 | 2/2018 | Pfeffer et al. |
| 9,962,085 B2 | 5/2018 | Griffith |
| 10,027,056 B1 | 7/2018 | Spangler |
| 10,029,090 B2 | 7/2018 | Shelton et al. |
| 10,033,296 B1 | 7/2018 | Lee |
| 10,149,933 B2 | 12/2018 | Bluvshtein et al. |
| 10,179,197 B2 | 1/2019 | Kaiser et al. |
| 10,232,185 B2 | 3/2019 | Tourrel et al. |
| 10,293,090 B2 | 5/2019 | Bonde et al. |
| 10,328,258 B2 | 6/2019 | Gittard et al. |
| 10,342,906 B2 | 7/2019 | D'Ambrosio et al. |
| 10,342,908 B2 | 7/2019 | Bluvshtein et al. |
| 10,342,983 B2 | 7/2019 | Nageri et al. |

(56) References Cited

U.S. PATENT DOCUMENTS

| | | | |
|---|---|---|---|
| 10,376,625 B2 | 8/2019 | Bluvshtein et al. | |
| 10,449,377 B2 | 10/2019 | Dearden et al. | |
| 10,512,553 B2 | 12/2019 | Griffith | |
| 10,646,646 B2 | 5/2020 | Ring et al. | |
| 10,652,740 B2 | 5/2020 | Rodriguez et al. | |
| 10,687,719 B2 | 6/2020 | Schmidt et al. | |
| 10,925,489 B2 | 2/2021 | Lee et al. | |
| 10,971,950 B2 | 4/2021 | Dearden et al. | |
| 11,027,114 B2 | 6/2021 | D'Ambrosio et al. | |
| 11,065,437 B2 | 7/2021 | Aber et al. | |
| 11,097,096 B2 | 8/2021 | Linden et al. | |
| 11,121,502 B2 | 9/2021 | Kasar et al. | |
| 11,154,706 B1 | 10/2021 | Fishel et al. | |
| 11,160,980 B2 | 11/2021 | Mishra et al. | |
| 11,165,196 B2 | 11/2021 | Yonnet et al. | |
| 11,185,677 B2 | 11/2021 | Salahieh et al. | |
| 11,324,940 B2 | 5/2022 | Earles et al. | |
| D967,408 S | 10/2022 | Tanaka et al. | |
| 11,471,663 B2 | 10/2022 | Tuval et al. | |
| 11,471,665 B2 | 10/2022 | Clifton et al. | |
| 2002/0044867 A1 | 4/2002 | Gharib et al. | |
| 2002/0087204 A1 | 7/2002 | Kung et al. | |
| 2003/0171642 A1 | 9/2003 | Schock et al. | |
| 2003/0233143 A1 | 12/2003 | Gharib et al. | |
| 2004/0151607 A1 | 8/2004 | Gharib et al. | |
| 2005/0228467 A1 | 10/2005 | Jiang | |
| 2006/0036127 A1 | 2/2006 | Delgado | |
| 2006/0202805 A1 | 9/2006 | Schulman et al. | |
| 2007/0177997 A1 | 8/2007 | Gharib et al. | |
| 2007/0208392 A1 | 9/2007 | Kuschner et al. | |
| 2008/0114339 A1 | 5/2008 | McBride et al. | |
| 2008/0132748 A1 | 6/2008 | Shifflette | |
| 2009/0248141 A1 | 10/2009 | Shandas et al. | |
| 2009/0259264 A1 | 10/2009 | Firth | |
| 2010/0241213 A1 | 9/2010 | Gharib et al. | |
| 2011/0034874 A1 | 2/2011 | Reitan et al. | |
| 2011/0046699 A1 | 2/2011 | Mazanec | |
| 2011/0257462 A1 | 10/2011 | Rodefeld et al. | |
| 2011/0282128 A1 | 11/2011 | Reitan et al. | |
| 2012/0053672 A1 | 3/2012 | Gharib et al. | |
| 2012/0059460 A1 | 3/2012 | Reitan | |
| 2013/0138205 A1* | 5/2013 | Kushwaha | A61F 2/82 623/1.26 |
| 2013/0289334 A1 | 10/2013 | Badstibner et al. | |
| 2013/0303831 A1 | 11/2013 | Evans | |
| 2014/0128659 A1 | 5/2014 | Heuring et al. | |
| 2015/0028805 A1 | 1/2015 | Dearden et al. | |
| 2015/0250935 A1 | 9/2015 | Anderson et al. | |
| 2016/0015879 A1 | 1/2016 | Gharib et al. | |
| 2016/0204544 A1 | 7/2016 | Liang et al. | |
| 2016/0206799 A1 | 7/2016 | Lucke et al. | |
| 2016/0303299 A1 | 10/2016 | Muller | |
| 2016/0303301 A1 | 10/2016 | Bluvshtein et al. | |
| 2016/0308403 A1 | 10/2016 | Bluvshtein et al. | |
| 2017/0087288 A1 | 3/2017 | Gross-Hardt et al. | |
| 2017/0112986 A1* | 4/2017 | Heuring | A61M 60/205 |
| 2017/0128014 A1 | 5/2017 | Hansen et al. | |
| 2017/0202513 A1 | 7/2017 | Schmidt et al. | |
| 2017/0266371 A1* | 9/2017 | Leonhardt | A61M 5/14276 |
| 2017/0312492 A1 | 11/2017 | Fantuzzi et al. | |
| 2017/0367820 A1* | 12/2017 | Anand | A61B 17/12131 |
| 2018/0055979 A1 | 3/2018 | Corbett et al. | |
| 2019/0125932 A1* | 5/2019 | Leonhardt | A61L 27/06 |
| 2019/0143018 A1* | 5/2019 | Salahieh | A61M 60/50 600/16 |
| 2019/0216995 A1 | 7/2019 | Kapur et al. | |
| 2019/0282805 A1 | 9/2019 | Schmidt et al. | |
| 2019/0290455 A1 | 9/2019 | Dearden et al. | |
| 2019/0358384 A1 | 11/2019 | Epple | |
| 2020/0000988 A1 | 1/2020 | Epple | |
| 2020/0023109 A1 | 1/2020 | Epple | |
| 2020/0023113 A1 | 1/2020 | Epple et al. | |
| 2020/0023158 A1 | 1/2020 | Epple | |
| 2020/0155844 A1 | 5/2020 | John et al. | |
| 2020/0179702 A1 | 6/2020 | Lee | |
| 2020/0197668 A1 | 6/2020 | Korkuch et al. | |
| 2020/0202990 A1 | 6/2020 | Liu et al. | |
| 2020/0222607 A1 | 7/2020 | El Katerji et al. | |
| 2020/0238056 A1 | 7/2020 | Fantuzzi | |
| 2020/0261633 A1 | 8/2020 | Spanier et al. | |
| 2020/0261719 A1 | 8/2020 | John et al. | |
| 2020/0269025 A1 | 8/2020 | Nitzan et al. | |
| 2020/0316379 A1 | 10/2020 | Yoo et al. | |
| 2021/0052893 A1 | 2/2021 | Suri et al. | |
| 2021/0077687 A1 | 3/2021 | Leonhardt | |
| 2021/0121624 A1 | 4/2021 | Greenberg et al. | |
| 2021/0187288 A1 | 6/2021 | Ng et al. | |
| 2021/0213283 A1 | 7/2021 | Yoo et al. | |
| 2021/0252286 A1 | 8/2021 | Boggs, II et al. | |
| 2021/0260360 A1 | 8/2021 | Georges et al. | |
| 2021/0288524 A1 | 9/2021 | Dearden et al. | |
| 2022/0080179 A1 | 3/2022 | Earles et al. | |
| 2022/0080182 A1 | 3/2022 | Earles et al. | |
| 2022/0080183 A1 | 3/2022 | Earles et al. | |
| 2022/0080184 A1 | 3/2022 | Clifton et al. | |
| 2022/0080185 A1 | 3/2022 | Clifton et al. | |
| 2022/0080186 A1 | 3/2022 | Clifton et al. | |

FOREIGN PATENT DOCUMENTS

| | | |
|---|---|---|
| BR | 102012024070 B1 | 8/2021 |
| EP | 1996252 B1 | 12/2008 |
| EP | 3351209 A1 | 7/2018 |
| EP | 2891239 B1 | 2/2019 |
| EP | 2962720 B1 | 1/2020 |
| EP | 3666805 A1 | 6/2020 |
| EP | 3711784 A1 | 9/2020 |
| EP | 3006072 B1 | 9/2021 |
| IN | 202117054744 A | 5/2022 |
| JP | 2017-035323 A | 2/2017 |
| WO | 1990/010471 A1 | 9/1990 |
| WO | 94/05347 A1 | 3/1994 |
| WO | 00/62838 A3 | 10/2000 |
| WO | 01/97908 A2 | 12/2001 |
| WO | 2002/103651 A1 | 12/2002 |
| WO | 2003/103745 A2 | 12/2003 |
| WO | 2006/062709 A3 | 6/2006 |
| WO | 2006/062710 A1 | 6/2006 |
| WO | 2009/157840 A1 | 12/2009 |
| WO | 2010/133567 A1 | 11/2010 |
| WO | 2013/148697 A1 | 10/2013 |
| WO | 2017/214118 A1 | 12/2017 |
| WO | 2018/045299 A1 | 3/2018 |
| WO | 2018/164902 A1 | 9/2018 |
| WO | 2019/140073 A1 | 7/2019 |
| WO | 2019/183247 A1 | 9/2019 |
| WO | 2020/061143 A9 | 5/2020 |
| WO | 2020/097428 A1 | 5/2020 |
| WO | 2020/132390 A1 | 6/2020 |
| WO | 2020/132554 A3 | 6/2020 |
| WO | 2020/150346 A1 | 7/2020 |
| WO | 2020/159921 A1 | 8/2020 |
| WO | 2020/185855 A1 | 9/2020 |
| WO | 2020/227521 A1 | 11/2020 |
| WO | 2021/062565 A2 | 4/2021 |
| WO | 2021/062566 A1 | 4/2021 |
| WO | 2021/113389 A1 | 6/2021 |
| WO | 2021/117021 A1 | 6/2021 |
| WO | 2021/119413 A1 | 6/2021 |
| WO | 2021/138673 A1 | 7/2021 |
| WO | 2021/184004 A1 | 9/2021 |
| WO | 2021/195135 A1 | 9/2021 |

OTHER PUBLICATIONS

Bourque et al. "HeartMate III: Pump Design for a Centrifugal LVAD with a Magnetically Levitated Rotor" ASAIO Journal. 47(4):401-405 (Jul. 2001).

Budris "Pump Performance Curve Shapes and How to Modify Them" (Jan. 2011) https://www.waterworld.com/technologies/pumps/article/16192402/pump-performance-curve-shapes-and-how-to-modify-them.

(56) References Cited

OTHER PUBLICATIONS

Chopski et al. "Mechanical Circulatory Support of the Right Ventricle for Adult and Pediatric Patients With Heart Failure" ASAIO Journal. 65(2):106-116 (Feb. 2019).
Curtas et al. "Computational Fluid Dynamics Modeling of Impeller Designs for the HeartQuest Left Ventricular Assist Device" ASAIO Journal. 48(5):552-561, (Sep.-Oct. 2002).
Du et al. "Electroactive shape memory polymer based on optimized multi-walled carbon nanotubes/polyvinyl alcohol nanocomposites" Composites Part B: Engineering, vol. 68, pp. 170-175 (Jan. 2015).
Gohean et al. "Scaling the Low-Shear Pulsatile TORVAD for Pediatric Heart Failure" ASAIO Journal. 63(2):198-206 (Mar./Apr. 2017).
Goldowsky, "Mini Hemoreliable Axial Flow LVAD With Magnetic Bearings: Part 2: Design Description" ASAIO Journal. 48(1):98-100 (Jan.-Feb. 2002).
Haddadi "Designing a More Effective Left Ventricular Assist Device Using CFD Simulation" (Jun. 2018) https://www.ansys.com/blog/designing-lvad-using-simulation.
Jagani et al. "Dual-Propeller Cavopulmonary Pump for Assisting Patients with Hypoplastic Right Ventricle" ASAIO Journal. 65(8):888-897 (Nov./Dec. 2019).
Lee "Long-Term Mechanical Circulatory Support System Reliability Recommendation by the National Clinical Trial Initiative Subcommittee" ASAIO Journal. 55(6):534-542 (Nov.-Dec. 2009).
Liu et al. "Review of electro-active shape-memory polymer composite" Composites Science and Technology, vol. 69, Issue 13, pp. 2064-2068 (Oct. 2009).
Locke et al. "Testing of a Centrifugal Blood Pump With a High Efficiency Hybrid Magnetic Bearing" ASAIO Journal. 49(6):737-743 (Nov.-Dec. 2003).
Mitamura et al. "A Durable, Non Power Consumptive, Simple Seal for Rotary Blood Pumps" ASAIO Journal. 47(4):392-396 (Jul. 2001).
Mountfort "Acute Cardiac Unloading and Recovery," Interventional Cardiology Review 2017; 12(2 Suppl 2):1-28.
Park et al. "Biologically Inspired, Open, Helicoid Impeller Design for Mechanical Circulatory Assist" ASAIO Journal. 66(8):899-908 (Aug. 2020).
Patil et al. "Effect of Geometrical Changes of Impeller on Centrifugal Pump Performance" nternational Research Journal of Engineering and Technology (IRJET) vol. 02 Issue: 02 (May 2015).
Schroeder "Balloon Catheters Over the Wire and Monorail," 2013 Peripheral Vascular Interventions: An Illustrated Manual, Article (4 pages) DOI: 10.1055/b-0034-65946.
Song et al. "Design and Transient Computational Fluid Dynamics Study of a Continuous Axial Flow Ventricular Assist Device" ASAIO Journal. 50(3):215-224 (May-Jun. 2004).
Tchantchaleishvili et al. "Clinical Implications of Physiologic Flow Adjustment in Continuous-Flow Left Ventricular Assist Devices" ASAIO Journal. 63(3):241-250 (May/Jun. 2017).
Throckmorton et al. "Controlled Pitch-Adjustment of Impeller Blades for an Intravascular Blood Pump" Journal. 58(4):382-389 (Jul./Aug. 2012).
Throckmorton et al. "Mechanical Cavopulmonary Assist for the Univentricular Fontan Circulation Using a Novel Folding Propeller Blood Pump" ASAIO Journal 53(6):734-741 (Nov.-Dec. 2007).
Throckmorton et al. "Uniquely Shaped Cardiovascular Stents Enhance the Pressure Generation of Intravascular Blood Pumps" The Journal of Thoracic and Cardiovascular Surgery, vol. 144, No. 3 (Sep. 2012).
Xie et al. "Strong Electroactive Biodegradable Shape Memory Polymer Networks Based on Star-Shaped Polylactide and Aniline Trimerfor Bone Tissue Engineering" ACS Applied Materials & Interfaces (Apr. 2015) 7 (12), 6772-6781, DOI: 10.1021/acsami.5b00191.
Xu et al. "Electro and Light-Active Actuators Based on Reversible Shape-Memory Polymer Composites with Segregated Conductive Networks" ACS Applied Materials & Interfaces (Jul. 2019) 11 (33), 30332-30340.
Bowler "This Wireless Heart Pump Battery Could Save Thousands of Lives" Science Alert (May 26, 2017).
Callington et al., "Computational fluid dynamic study of hemodynamic effects on aortic root blood flow of systematically varied left ventricular assist device graft anastomosis design," J. Thorac Cardiovasc Surg., 150(3):696-704 (Sep. 2015).
Doersch "Temporary Left Ventricular Assist Device Through an Axillary Access is a Promising Approach to Improve Outcomes in Refractory Cardiogenic Shock Patients," Asaio J., 61(3):253-258 (May-Jun. 2015).
Esposito et al., "Acute mechanical circulatory support for cardiogenic shock: the 'door to support' time," F1000Research, 6:737 (2017).
Esposito et al., "Left Ventricular Unloading Before Reperfusion Promotes Functional Recovery After Acute Myocardial Infarction" Journal of the American College of Cardiology, 72(5):501-514 (Jul. 31, 2018).
Gershgorn "Your Wireless Internet Could Power Your Future Devices" Popular Science, (https://www.popsci.com/your-wireless-internet-could-power-your-future-devices) (Jun. 3, 2015).
Gohean et al., "Preservation Of Native Aortic Valve Flow And Full Hemodynamic Support With The TORVAD(Trademark) Using A Computational Model Of The Cardiovascular System," Asaio J., 61(3):259-265 (May-Jun. 2015).
Ho et al., "Midfield Wireless Powering for Implantable Systems," Proceedings of the IEEE, pp. 1-10 (2013 IEEE).
ICR "Acute Cardiac Unloading and Recovery," Interventional Cardiology Review, 12(2 Suppl 2):1-281 (2017).
International Search Report for International Application No. PCT/US19/23208, dated Jul. 5, 2019, 5 pages.
International Written Opinion for International Application No. PCT/US19/23208, dated Jul. 5, 2019, 6 pages.
Kapur et al., "Mechanically Unloading the Left Ventricle Before Coronary Reperfusion Reduces Left Ventricular Wall Stress and Myocardial Infarct Size," Circulation., 128. 10.1161/CIRCULATIONAHA.112.000029 (Jun. 2013).
Keeble et al., "Percutaneous haemodynamic and renal support in patients presenting with decompensated heart failure: A multicentre efficacy study using the Reitan Catheter Pump (RCP)" Int. J. Card., 275:53-58 (2019).
Knecht et al., "High Efficiency Transcutaneous Energy Transfer for Implantable Mechanical Heart Support Systems" IEEE Transactions On Power Electronics, 30(11) (Nov. 2015).
Kormos et al., "Left Ventricular Assist Device Malfunctions: It's More Than Just The Pump," CIRCULATIONAHA.117.027360, originally published (Jul. 3, 2017).
Langston "Popular Science names 'Power Over Wi-Fi' one of the year's game-changing technologies," UW News, (http://www.washington.edu/news/2015/11/18/popular-science-names-power-over-wi-fi-one-of-the-years-game-changing-technologies/) (Nov. 18, 2015).
MacFelda et al., "Bioelectrical signals improve cardiac function and modify gene expression of extracellular matrix components" ESC Heart Failure 2017; 4: 291-300 (published online Jun. 30, 2017).
Pahlevan et al., "A Bio-Inspired Approach for the Reduction of Left Ventricular Workload," PLOSone, (Jan. 24, 2014).
Pahlevan et al., "A wave dynamics criterion for optimization of mammalian cardiovascular system," J. Biomech., 47(7):1727-32 (May 2014).
Pahlevan et al., "Aortic Wave Dynamics and Its Influence on Left Ventricular Workload," PLOSone, (Aug. 11, 2011).
Palma et al., "Pulsatile stent graft: a new alternative in chronic ventricular assistance," Revista Brasileira de Cirurgia Cardiovascular, 28(2):217 (2013).
Queensland University of Technology "Wireless system to power heart pumps could save lives currently lost to infection," (May 15, 2017, Queensland University of Technology), https://phys.org/news/2017-05-wireless-power-heart-lost-infection.html.
Saku et al., "Total Mechanical Unloading Minimizes Metabolic Demand of Left Ventricle and Dramatically Reduces Infarct Size in Myocardial Infarction," https://doi.org/10.1371/journal.pone.0152911 (2016).
Second Heart, Temporary and chronic circulatory assist devices, Int. J. Card., 2018; 275 (2019) 53-58.

(56) References Cited

OTHER PUBLICATIONS

Watanabe et al., "Left Ventricular Unloading Using an Impella CP Improves Coronary Flow and Infarct Zone Perfusion in Ischemic Heart Failure," J. Am. Heart Assoc., 7:e006462 (2018).
WiFi Boosters, Repeaters and Extenders RepeaterStore, (https://www.repeaterstore.com/pages/wifi-booster-repeater-extender-differences) (accessed Feb. 26, 2018).
Brancato et al. "An Implantable Intravascular Pressure Sensor for a Ventricular Assist Device." Micromachines vol. 7, 8 135. Aug. 8, 2016, doi:10.3390/mi7080135.
Loeb et al. "Bion system for distributed neural prosthetic interfaces" Medical Engineering and Physics, 23(1):9-18, Jan. 2001.
Skori Webste "Interesting Connections" 20 pages with English translation, accessed Jan. 11, 2022 http://skory.gylcomp.hu/kapcs/.
Bartoli et al. "The Future of Adult Cardiac Assist Devices: Novel Systems and Mechanical Circulatory Support Strategies" Cardiol Clin. Nov. 2011 ; 29(4): 559-582. doi:10.1016/j.ccl.2011.08.013.
Courboulin et al. "Increasing Pulmonary Artery Pulsatile Flow Improves Hypoxic Pulmonary Hypertension in Piglets" Journal of Visualized Experiments JoVE ,99 e52571. (May 2015) 9 pages, doi:10.3791/52571.
Henaine et al. "Effects of lack of pulsatility on pulmonary endothelial function in the Fontan circulation" The Journal of Thoracic and Cardiovascular Surgery vol. 146, Issue 3, Sep. 2013, pp. 522-529.
Metagadget Editors "New Wireless Heart Pump Makes No Contact with Blood" https://www.medgadget.com/2016/06/new-wireless-heart-pump-makes-no-contact-blood.html (Jun. 27, 2016).
Naeije (1991) Pulsatile Flow Pulmonary Hemodynamics. In: Vincent J.L. (eds) Update 1991. Update in Intensive Care and Emergency Medicine, vol. 14. Springer, Berlin, Heidelberg, https://doi.org/10.1007/978-3-642-84423-2_33.
Reuben "Compliance of the Human Pulmonary Arterial System in Disease" Circulation Research, vol. XXIX, pp. 40-50 (Jul. 1971).
Thenappan et al. "The Critical Role of Pulmonary Arterial Compliance in Pulmonary Hypertension." Annals of the American Thoracic Society, vol. 13, No. 2 (Feb. 2016) pp. 276-284. doi:10.1513/AnnalsATS.201509-599FR.
UCLA (University of California, Los Angeles) Health Sciences. "Lung transplant recipient defies all odds: New approach to oxygenation helps patient live long enough for surgery." ScienceDaily. ScienceDaily, Jul. 6, 2012 www.sciencedaily.com/releases/2012/07/120706151904.htm>.
European Search Report and Search Opinion Received for EP Application No. 19772334, dated Nov. 29, 2021, 7 pages.
Lee "A Capacitor-Based AC-DC Step-Up Converter for Biomedical Implants" Proc. of the IEEE 2011 Custom Integrated Circuits Conference, paper 8.6 (Sep. 2011).
Lee "An Inside Body Power and Bidirectional Data Transfer IC Module Patent Application Information Retrieval (PAIR)" IEEE Journal of Solid-State Circuits, vol. 46, No. 8, pp. 1820-1831 (Aug. 2011).
Lee et al. "A Biomedical Implantable FES Battery-Powered Micro-Stimulator" IEEE Transactions on Circuits and Systems—I: Regular Papers, vol. 56, No. 12 (Dec. 2009).
Schulman "The Feasible FES System: Battery Powered BION Stimulator" Proceedings of the IEEE, vol. 96, No. 7, pp. 1-14 (Jul. 2008).
Schulman et al. "An Implantable Bionic Network of Injectable Neural Prosthetic Devices: The Future Platform for Functional Electrical Stimulation and Sensing to Restore Movement and Sensation" J. P. Mobley, J. Wolfe, R. Davis, I. Arcos, In Neuroengineering, D. J. DeLorenzo and J.D. Bronzino, Eds., 18: 1-16 (2008). CRC Press, Chapter.
Shimada et al. "Electrical stimulation using implantable radiofrequency microstimulators to relieve pain associated with shoulder subluxation in chronic hemiplegic stroke" Neuromodulation 9(3):234-8 (2006).
Chakroborty "Controllable Pitch Propeller (CPP) Vs Fixed Pitch Propeller (FPP)" Naval Architecture (Last updated Jun. 14, 2021) Accessed Feb. 24, 2022 https://www.marineinsight.com/naval-architecture/controllable-pitch-propeller-cpp-vs-fixed-pitch-propeller-fpp/.
Wikipedia "Variable-pitch propeller (aeronautics)" Accessed Feb. 24, 2022 https://en.wikipedia.org/wiki/Variable-pitch_propeller_(aeronautics).
Wikipedia "Variable-pitch propeller (marine)" Accessed Feb. 24, 2022 https://en.wikipedia.org/wiki/Variable-pitch_propeller_(marine).
Feldman et al. "Transcatheter Interatrial Shunt Device for the Treatment of Heart Failure With Preserved Ejection Fraction (Reduce LAP-HF I [Reduce Elevated Left Atrial Pressure in Patients With Heart Failure])" Circulation, 137:364-375 (Nov. 15, 2017).
Hemodynamic Talk—New Mechanical Circulatory Support for High Risk PCI, Slide Show Presentation, accessed Nov. 5, 2021 https://slidetodoc.com/hemodynamic-talk-new-mechanical-circulatory-support-for-high/.
Rosset et al. "Mechanical properties of electroactive polymer microactuators with ion-implanted electrodes" Proc. of SPIE vol. 6524 652410-11 (Apr. 2007).
Vora et al. "First-in-human experience with Aortix intraaortic pump" Catheterization and Cardiovascular Interventions vol. 93, Issue 3 p. 428-433 (Oct. 11, 2018).
European Extended Search Report and Opinion for European Application No. 19772334.9, dated Nov. 19, 2021, 7 pages.
Benjamin et al "Heart Disease and Stroke Statistics—2019 Update, A Report from the American Heart Association" Circulation, Mar. 2019;139:e56-e528.
Idata Research "Over 965,000 Angioplasties (PCIs) are Performed Each Year in the United States" Jul. 10, 2020.
Japanese Notice of Reasons for Refusal for Japanese Application No. 2021-500488, dated Nov. 22, 2021, 6 pages with English translation.
Roger et al. "Heart Disease and Stroke Statistics—2011 Update: A Report From the American Heart Association" Circulation. Feb. 1, 2011; 123(4): e18-e209. doi:10.1161/CIR.0b013e3182009701.
Ronco et al. "Cardiorenal Syndrome in Western Countries: Epidemiology, Diagnosis and Management Approaches" Kidney Diseases, 2:151-163, Sep. 10, 2016.
Baric, Why pulsatility still matters: a review of current knowledge Croatian Med. J. vol. 55(6), Dec. 2014, pp. 609-620.
Abate "Stanford engineer invents safe way to transfer energy to medical chips in the body" Stanford University Engineering Magazine Article, accessed Aug. 15, 2022 at https://protect-us.mimecast.com/s/j1E3C9rp2PT1AgQC1iHgV?domain=forum.stanford.edu.
Choi "Wireless Power Transfer Will Energize Our Implants" Popular Mechanics Article, last accessed Aug. 15, 2022, https://www.popularmechanics.com/science/health/a10553/wireless-power-transfer-will-energize-our-implants-16807980/#:~:text=Using%20wireless%20power%20transfer%20to%20get%20energy%20to,name%20suggests%2C%20they%20cannot%20transfer%20power%20very%20far.%22.
Khan et al. "Wireless Power Transfer Techniques for Implantable Medical Devices: A Review" Sensors (Jun. 2020), 20, 3487; doi:10.3390/s20123487 www.mdpi.com/journal/sensors.
Simich "World-first wireless electricity supply headed for consumers" accessed Aug. 15, 2022 from https://www.eit.edu.au/world-first-wireless-electricity-supply-headed-for-consumers/.
Stanford University Poster slides "Midfield Powering for Implantable Systems" Stanford Integrated Biomedical Systems, 9 pages.

* cited by examiner

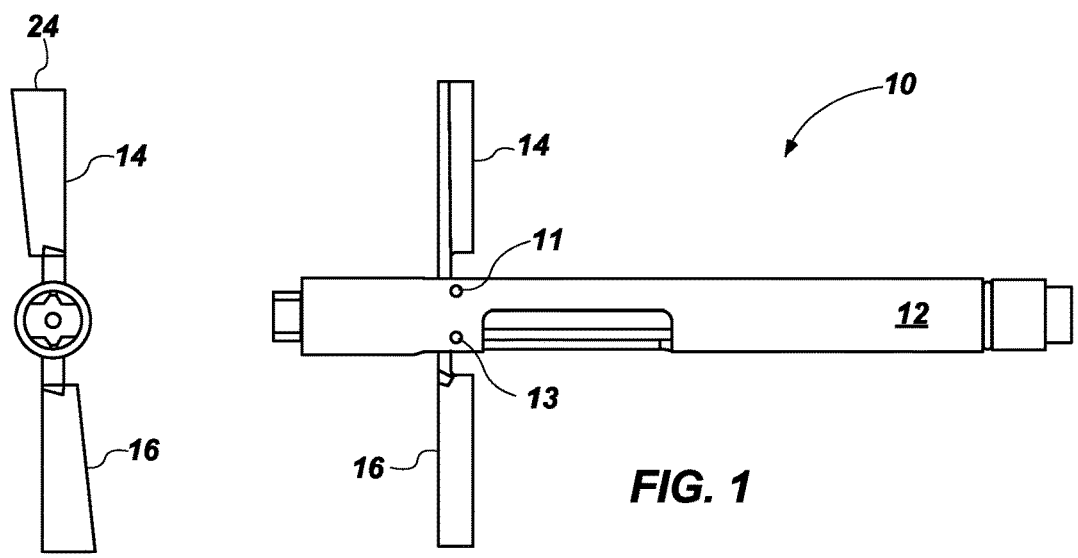
FIG. 3
FIG. 1
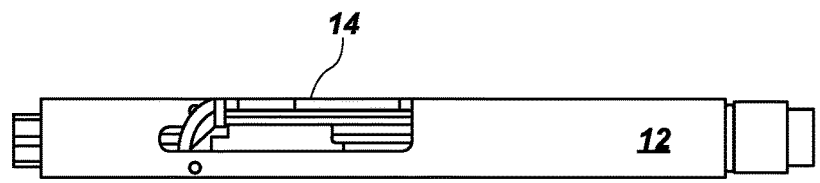
FIG. 2
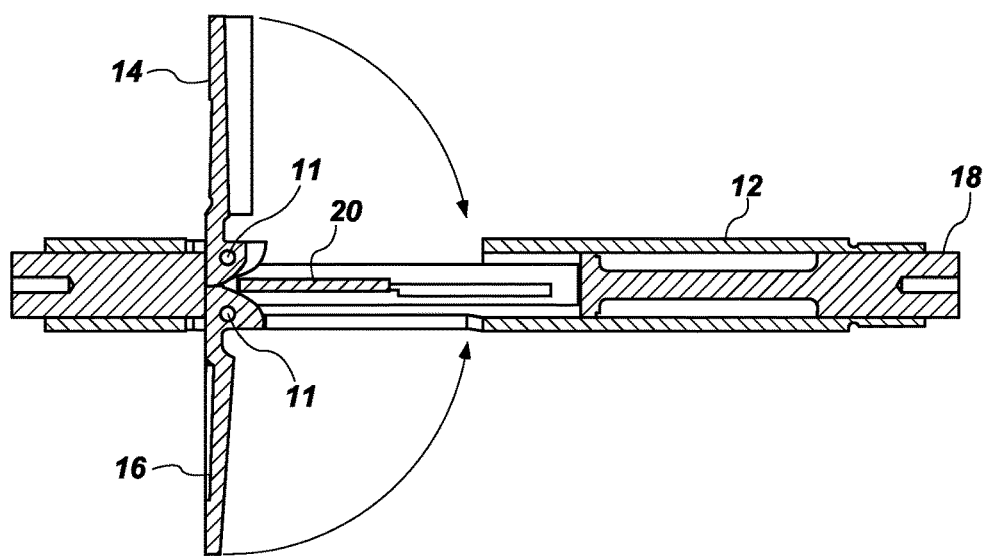
FIG. 4

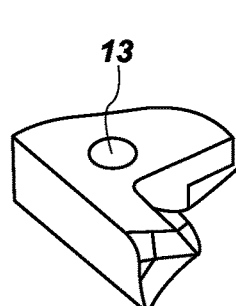
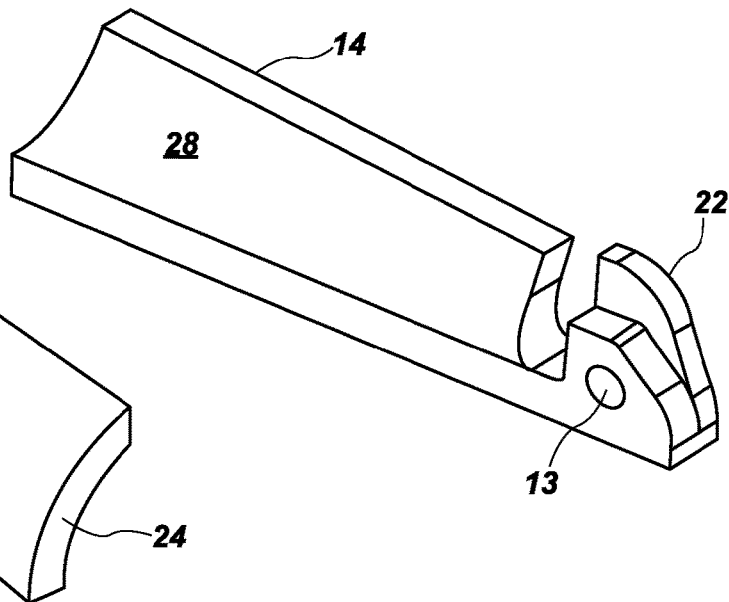
FIG. 5  FIG. 6
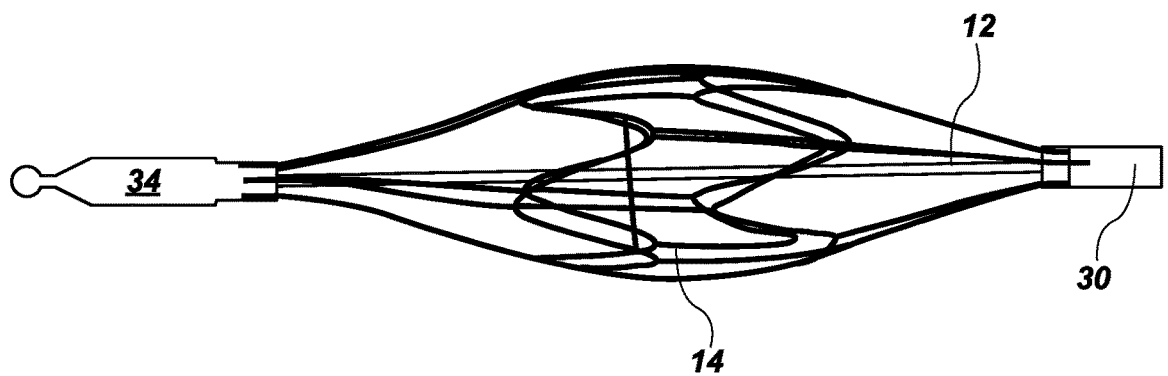
FIG. 7

CIRCULATORY ASSIST PUMP

CROSS-REFERENCE TO RELATED APPLICATIONS

This application is the national phase entry under 35 U.S.C. § 371 of International Patent Application PCT/US2019/023208, filed Mar. 20, 2019, designating the United States of America and published as International Patent Publication WO 2019/183247 A1 on Sep. 26, 2019, which claims the benefit of U.S. provisional patent application 62/645,599, filed Mar. 20, 2018; U.S. provisional patent application 62/682,046, filed Jun. 7, 2018; U.S. provisional patent application 62/694,564, filed Jul. 6, 2018, the contents of the entirety of each of which are hereby incorporated herein by this reference.

TECHNICAL FIELD

The disclosure relates generally to medical devices, and more particularly to a system, apparatus, and associated methods for assisting a subject's heart to pump blood (e.g., a circulatory assist pump).

BACKGROUND

U.S. Pat. No. 8,617,239 to Reitan (Dec. 13, 2013), the contents of which are incorporated herein by this reference, relates to a catheter pump to be positioned in the ascending aorta near the aortic valve of a human being, comprising an elongated sleeve with a drive cable extending through the sleeve and connectable at its proximal end to an external drive source and a drive rotor near the distal end of the drive cable mounted on a drive shaft being connected with the drive cable. The drive rotor consists of a propeller enclosed in a cage and the propeller and the cage are foldable from an insertion position close to the drive shaft to an expanded working position, which are characterized by means for anchoring the drive rotor in the ascending aorta near the aortic valve after insertion. Also described is a method to position the pump of a catheter pump in the ascending aorta just above the aortic valve.

U.S. Pat. No. 8,617,239 to Reitan builds upon an earlier patent of Reitan, i.e., U.S. Pat. No. 5,749,855 to Reitan (May 12, 1998), the contents of which are also incorporated herein by this reference, which relates to a drive cable, with one end of the drive cable being connectable to a drive source and a collapsible drive propeller at the other end of the drive cable. The collapsible drive propeller is adjustable between a closed configuration in which the collapsible drive propeller is collapsed on the drive cable and an open configuration in which the collapsible drive propeller is expanded so as to be operative as an impeller. A sleeve extends between one side of the collapsible drive propeller and the other side of the collapsible drive propeller with the sleeve being movable between configurations in which the collapsible drive propeller is in the open and closed configuration. A lattice cage is arranged surrounding the propeller and is folded out at the same time as the propeller.

As described by U.S. Pat. No. 8,617,239 to Reitan, while the device of U.S. Pat. No. 5,749,855 operates very well in many circumstances, there is still room for improvement. For example, it would be safer if the lattice cage folded out before the propeller folded out. In addition, the shaft supporting the propeller needs to be journaled with bearings, and such bearings require lubrication.

An even earlier blood pumping catheter is described in U.S. Pat. No. 4,753,221 to Kensey et al. (Jun. 28, 1988), the contents of which are incorporated herein by this reference. Kensey et al. relates to an elongated catheter for pumping blood through at least a portion of a subject's vascular system. The catheter is of a sufficiently small diameter and flexibility to enable it to be passed through the vascular system so that the distal end portion of the catheter is located within or adjacent the patient's heart. A rotatable pump is located at the distal end of the catheter and is rotated by drive means in the catheter. The distal end portion of the catheter includes an inlet for blood to flow therein and an outlet for blood to flow therefrom. The catheter is arranged so that blood is pumped by the catheter's pump through the heart and into the vascular system without requiring any pumping action of the heart.

Other catheter pumps are known from US 2008/0132748 A1, US 2008/0114339 A1, and WO03/103745A2, the contents of each of which are incorporated herein by this reference.

BRIEF SUMMARY

Described, among other things, is a minimally invasive circulatory support platform that utilizes an aortic stent pump. The platform uses a low profile, catheter-based technique and can be used to provide temporary and chronic circulatory support depending on the needs of the subject or patient (e.g., a mammal, such as a human).

In certain embodiments, the described device includes a temporary circulatory assist pump on the tip of an aortic catheter.

In certain embodiments, the device includes a further pump placed intermediate between the catheter tip and herein described handle for placement of the further pump in the aorta, right above the renal arteries.

In certain embodiments, the described device includes a wireless powered circulatory assist pump (or pumps) positioned within an aortic stent.

Also described is a catheter-based, temporary circulatory assist pump (e.g., powered by an associated endovascular catheter with a drive) for use in treating a patient with acute decompensated heart failure, which pump provides circulatory support to a subject undergoing high risk percutaneous coronary intervention ("PCI"). Such a temporary circulatory support pump is typically placed within an aortic stent on the tip of a catheter placed just above the renal arteries in the descending aorta. The catheter is of sufficiently small diameter and flexibility to enable it to be passed through the vascular system so that the distal end portion of the catheter can be appropriately placed within the aorta. This reduces workload on a patient's heart, and improves lower extremity perfusion.

When the catheter is disconnected from the stent after placement in the aorta, the stent can be switched to wireless power. The wireless electromagnetic power communicates directly with, e.g., iron filled (+) and (−) polarized tips of impeller blades. The pump may be combined with a removable wireless powered pulsatile mesh stent, which is placed above the catheter higher in the aorta. QUT repeater technology may be included for enhanced wireless power. "Wireless system to power heart pumps could save lives currently lost to infection," (May 15, 2017, Queensland University of Technology), https://phys.org/news/2017-05-wireless-power-heart-lost-infection.html, the contents of which are incorporated herein by this reference.

Further described is a wirelessly powered circulatory assist pump (an aortic stent implant) that provides chronic circulatory support for heart failure patients. A wireless powered chronic implant can be removable and can utilize both continuous and pulsatile flow.

The described platform and system are relatively easy to place, have higher flow rates than existing systems, and provide improvements in a patient's renal function. The chronic circulatory assist device (which is removable) is placed within an aortic stent that is preferably wirelessly powered, and combined with, e.g., a vibrational harmonic energy technology or electric charge surface treatment to reduce or prevent blood clot (thrombus) formation, which may be associated with the device. Such a system features both a rotating impeller within a lower positioned aortic stent and a pulsating cuff aortic stent, which is placed above the primary stent pump. The impeller is shaped and designed to maximize safety and blood flow and to reduce the risk of hemolysis. Also described is a low RPM impeller system that displays higher flow, less heat, and less hemolysis risk for the patient.

Further described is a platform that may be used to provide circulatory assist support by maximizing cardio and renal function recovery, while at the same time minimizing risk of thrombosis, stroke, hemolysis, mechanical breakdown, infection, and heart valve damage. Further, because the impeller is positioned relatively far from the heart (e.g., just above the renal arteries in the aorta, see *Int. J. Card.* 2018; 275 (2019)53-58), the natural pulsatility of a heart beat is maintained. The impeller simply works in cooperation and harmony with the pulse waves. In contrast, prior art placement within or near the heart interferes with natural pulsatility. Preferably, flow and energy use are optimized via timing of pulsations and impeller turn speeds with natural heart pulsatile flow.

The system or "loop" may be automatically read and adjusted to maximize power usage, battery life, long term durability, flow, and patient blood pressure(s) that self-adjusts automatically in response to changing conditions of the patient such as sleep and exercise.

Particularly described is, e.g., a catheter-based circulatory assist pump and methods of using it. Such a pump assists the subject's heart's pump function. The circulatory assist pump is primarily intended for use in assisting a subject suffering from heart failure.

Also particularly described is a circulatory assist pump intended for implantation that comprises a tubular elongated casing, which is associated with a plurality of impellers, which fold and extend therefrom, through which a shaft passes. The shaft has means (e.g., an actuation cable and/or associated cam system) that extends the impeller arm-like blades perpendicularly and preferably also retracts them. Because of the outwardly-foldable arm-like impeller blades, the catheter can be made very narrow, which is advantageous during introduction or implantation into the subject's circulatory system, but nevertheless provides a powerful flow effect when the blades are in their extended condition.

In use, the catheter may be introduced "percutaneously" into the lower aorta via, e.g., the normal "Seldinger technique" in the groin (a small incision into the femoral artery) and fed up to the aorta to the desired position (e.g., the descending aorta). The pump may be inserted in the groin area and introduced into the femoral artery (e.g., to just above the renal arteries in the descending aorta) with the help of a small surgical insertion and insertion sheath. The pump is thereafter fed up into the desired position in the lower aorta.

Alternatively, the pump may be placed via axillary entry in the neck or chest of the subject. See, e.g., K M. Doersch "Temporary Left Ventricular Assist Device Through an Axillary Access is a Promising Approach to Improve Outcomes in Refractory Cardiogenic Shock Patients," *ASAIO J.* 2015 May-June; 61(3): 253-258; doi: 10.1097/MAT.0000000000000222, the contents of which are incorporated herein by this reference, which describes implantation of a temporary left ventricular assist device ("LVAD") through an axillary approach as a way to provide adequate circulation to the patient, avoid multiple chest entries and infection risks.

Treatment will typically continue for six (6) hours, but may last, for example, for 72 hours.

A preferred embodiment utilizes a monorail guidewire lumen "rapid exchange" ("RX") system, where the guidewire lumen may extend proximally only. See, e.g., US 2003/0171642 A1 to Schock et al. (Sep. 11, 2003) and J. Schroeder 2013 *Peripheral Vascular Interventions: An Illustrated Manual*, "Balloon Catheters Over the Wire and Monorail," DOI: 10.1055/b-0034-65946, the contents of each of which are incorporated herein by this reference.

In order to avoid the impeller damaging the surrounding tissue, the pump is preferably encased within a cage, stent, or "stent cage" that shields, e.g., the subject's aortic tissue from the impeller. The (aortic) stent cage preferably has a highly open flow. It is sized and made of a material that provides for stability against the aortic wall of the subject, where it is preferably strongly affixed to the aortic wall. Preferably, the aortic stent cage has just the right radial force to distend the aorta, for example, two (2) mm, giving extra flow and a safety area and which stabilizes position of pump securely (other systems like Procyrion™ reportedly migrate up with the motor "on" and down with the motor "off"). A gap between the aortic stent/protective cage and the aorta wall allows for back and forth motion, which increases turbulence of flow and increasing the risk of dislodging thrombus from the aortic wall, and causing much more damage than secure fixation. Furthermore, flow thrust is lost when the tip bounces back and forth in the aorta, which is reduced with the instant design.

A wireless drive is preferably utilized to drive the pump. Such a drive is typically in the form of an external power belt (electric powered copper coil inside) and appropriate circuitry that fits around the patient's abdomen, which belt provides a magnetic field that drives and/or controls rotation of the impeller.

The impeller blades' tips preferably comprise a material subject to magnetic forces. The impeller can also be provided with an elastic rubber sheath (not shown) which reduces tissue damage and which can also increase the pressure effect.

In certain embodiments, sensors are used with the system, e.g., to monitor hemolysis and/or impeller speed, and the pulsations of cuffs are adjusted as desired to balance a minimization of hemolysis with a maximization of flow utilizing the system.

In certain embodiments, a pulsating stent graft in the patient's upper aorta and an impeller turning circulatory assist pump placed in a bare aortic stent in the patient's lower aorta may be used in combination, with timing optimized. For instance, appropriately placed sensors may be used to optimize the timing of pulsations of the upper aortic stent graft and the revolutions per minute of a lower bare aortic stent impeller circulatory assist pump.

In order to avoid thrombo-embolismic complications, the circulatory assist pump or parts thereof can be, e.g., heparinized.

The actuation cable can be in the form of a compact cable that runs through the tubular elongated casing of the catheter. The actuation cable has such a construction that the impeller folds outwardly with forward movement of the actuation cable by the physician.

The tubular elongated casing can be surrounded by a sleeve or a tube of an elastic material such as rubber or similar.

In its extended condition, the impeller preferably has a working diameter about 23 mm for an adult human.

In practice, the described system may be used to not only sustain a (e.g., congestive heart failure) patient's life, but also may be used to provide mechanical circulatory assistance for, e.g., up to 36 months, during the course of heart rehabilitation/regeneration treatment.

The described system offers advantages over existing heart assist devices in that it need not cross the aortic valve, and location positioning of the device is not as strict as with existing devices, meaning there is less need to reposition the device. Furthermore, the system maintains arterial pulsatility, does not require a high pump speed (e.g., 7,500 vs. 33,000 rpm), reduces hemolysis, and reduces acute kidney injury.

BRIEF DESCRIPTION OF THE DRAWINGS

FIG. 1 depicts a lobe design according to the instant disclosure displaying deployed (or extended) arm-like impeller blades.

FIG. 2 depicts the lobe design of FIG. 1 displaying retracted arm-like impeller blades.

FIG. 3 depicts a front view of the lobe design of FIG. 2 displaying deployed (operational) impellers.

FIG. 4 is a cross-sectional view of the device of FIG. 1.

FIGS. 5 and 6 show an impeller blade's shape.

FIG. 7 depicts a stent cage, at the tip of the catheter, which surrounds the arm-like impeller blades, where, e.g., a wirelessly driven impeller is contained within a protective cage stent.

DETAILED DESCRIPTION

Figure 8:
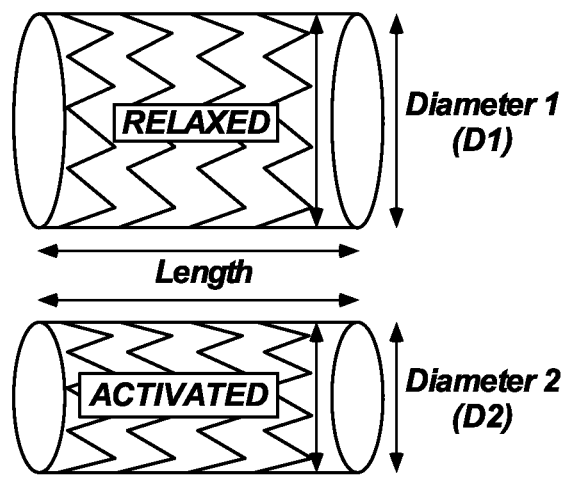
FIG. 8 depicts the prior art pulsatile stent of the incorporated herein Palma et al.

An aspect of the disclosure is a circulatory assist pump, generally 10, shown in FIGS. 1, 3, and 4 in its operational position. The circulatory assist pump 10 comprises a tubular elongated casing 12 associated with a pair of arm-like impeller blades 14, 16. The depicted impeller blades are pivotally associated with the remainder of the lobe by pivots (e.g., pins or shafts) 11 placed in apertures 13 in the tubular elongated casing 12 and impeller blades. The impeller blades are outwardly foldable and retractable, and can move, e.g., into a position perpendicular to the tubular elongated casing 12. As can be determined, the accompanying figure drawings are generally not drawn to scale.

The depicted circulatory assist pump includes a positioning cable 18 running along the impeller axis, about which the impeller blades 14, 16 (along with the rest of the device) rotate to create a pump action, for example, in the aorta. The arm-like nature of the depicted blades allows them to extend maximally from the remainder of the body when in a perpendicular position and fill a large portion of the descending aorta. At the end of the positioning cable is a rod 20 that interacts with a cam portion 22 of each impeller blade (see, e.g., FIGS. 4 and 6). Advancing (or relatively displacing) the rod 20 so that it abuts and actuates the cam portion 22 causes the withdrawn impeller (FIG. 3) to extend outwards from the rest of the lobe (FIG. 1). The cam lobe design (FIG. 4) is utilized to expand and retrieve the impeller into and out of the catheter, which is far more reliable deployment than with, for example, a spring design, although a spring may also be used herein. For example, springs vary with temperature and manufacturing, while cam lobes are consistent and remain constant.

As depicted in FIGS. 5 and 6, each impeller blade has a tip 24, face 26, and back 28 (any or all of which may be magnetic so as to be driven by a wireless drive). The impeller shape design as depicted in FIGS. 5 and 6 maximizes blood flow at low power/lower RPMs, while reducing hemolysis and heat. Lower RPMs mean less power needs, improving a system powered wirelessly. There is also reduced risk of a mechanical breakdown. Materials that can be magnetized, which are also the ones that are strongly attracted to a magnet, are called ferromagnetic (or "ferrimagnetic"). Such materials include iron, nickel, cobalt, some alloys of rare-earth metals, and some naturally occurring minerals.

In certain embodiments, the impeller blades can be tilted on demand (in the same manner as the way an airplane wing flaps are controlled) by, e.g., adjustment of the cams, which balances hemolysis, thrust, and flow; maximizes flow with a temporary increase in hemolysis; and can be used to catch native aortic flow to re-charge a battery in the center spindle.

An aortic stent cage surrounds the impeller (see, e.g., FIGS. 7, 11, and 14-17) and preferably has the most open area possible (see, e.g., FIG. 15), so as to reduce hemolysis. The system thus matches greater strength and protection in balance. The wire-like elements of the stent cage are preferably rounded and are not too thin (like razor wire that can cut blood cells) or too thick like the prior art's flat elements, which can smack hard against and damage blood cells (hemolysis) on their flat surface planes. The depicted aortic stent protective cage with high flow through areas has rounded elements and balance stability strength with low hemolysis and high flow. Preferably, the aortic stent has strength and not too many flat cage elements to damage blood cells and inhibit flow. This may be achieved by use of the rounded cage elements and by design permitting high radial force and strength (certain prior art devices do not even reach the aortic wall (e.g., <20 mm in an adult human) and bounce back and forth in large aortas).

Prior art devices have been known to migrate up and down and bounce side to side in the aorta. Their flow is disturbed and energy is lost in the process. Their movement causes turbulence, which promotes blood clotting and hemolysis.

An aortic stent as described herein (see, e.g., FIG. 17) can be detached from the associated drive shaft and external motor controller (which are removed from the patient) and can be converted to wireless power. For example, instead of being driven by the drive axis, the pump can then be powered via, e.g., an external belt system or wireless power WiFi in the patient's home or workplace.

The system is preferably positioned and stabilized in the aorta and the available impeller space is widened with a high radial force aortic stent that distends the aortic wall inner diameter, for example, about two (2) mm. Such positioning allows more flow and more use of the entire area of the aorta, particularly in comparison to the prior art. Such aortic stent strength stabilizes position and reduces the need for repositioning.

In preferred embodiments, a confirming high radial force aortic stent provides for firm stability of fixation of position without the need for hooks. Such a system distends the diameter of the aorta by about two (2) mm (on average), which provides more space available for impeller use.

The expandable stent may be manufactured and adapted for use herein in accordance with techniques known by those of skill in the art (see, e.g., U.S. Pat. No. 5,354,308 to Simon et al. (Oct. 11, 1994), U.S. Pat. No. 4,580,568 to Cesare Gianturco (Apr. 8, 1986), and U.S. Pat. No. 5,957,949 to Leonhardt et al. (Sep. 28, 1999), the contents of each of which are incorporated herein by this reference).

Depicted is a circulatory assist pump within a bare aortic stent at the tip of a 13.8 French ("FR") catheter for temporary support. The aortic stent with impeller (e.g., FIG. 7) may be driven by a drive line associated with the placement catheter 30, or disconnected from the catheter and switched to wireless power. In the embodiment of FIG. 7, there is a simple impeller in the stent cage on tip of the catheter with vibrational energy delivered via the drive shaft.

In certain embodiments, the catheter protective cage aortic stent expands and compresses easily, e.g., to pass another catheter by the stent cage. For example, a standard PCI catheter was run up the outside of the stent cage and was of no issue. The radial force of the stent is insufficient to collapse the PCI catheter, particularly when placed against a compliant aorta. The stent typically presses the PCI catheter about 1 mm into the aorta wall and leaves open the whole aorta for the impeller with a large safety gap. The impeller may be angled down like arrow feathers, and then there is even more room for placing a PCI catheter.

Figure 14:
FIG. 14 depicts a "Biomerics Advanced Catheter" having a catheter, catheter connector, drive shaft, handle, impeller, stent cage, and tip.

The protective cage opens and closes relatively easily with a simple turn of the wheel on a handle associated with the catheter (FIG. 14). Collapsing it partially (or fully) allows for the passage of the PCI catheter and then may be opened up fully when the PCI catheter is in place.

Figure 15:
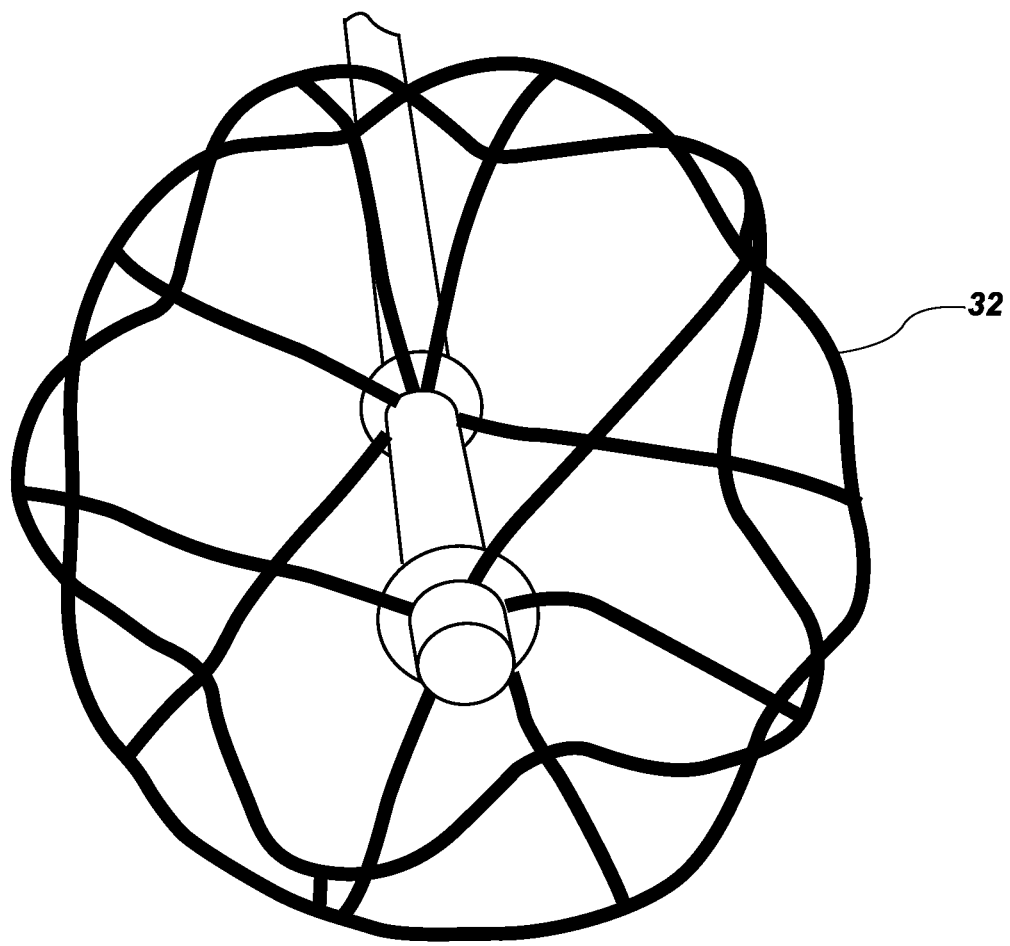
FIG. 15 depicts a front view of the stent cage of FIG. 7 showing the highly open design of the cage.
Figure 16:
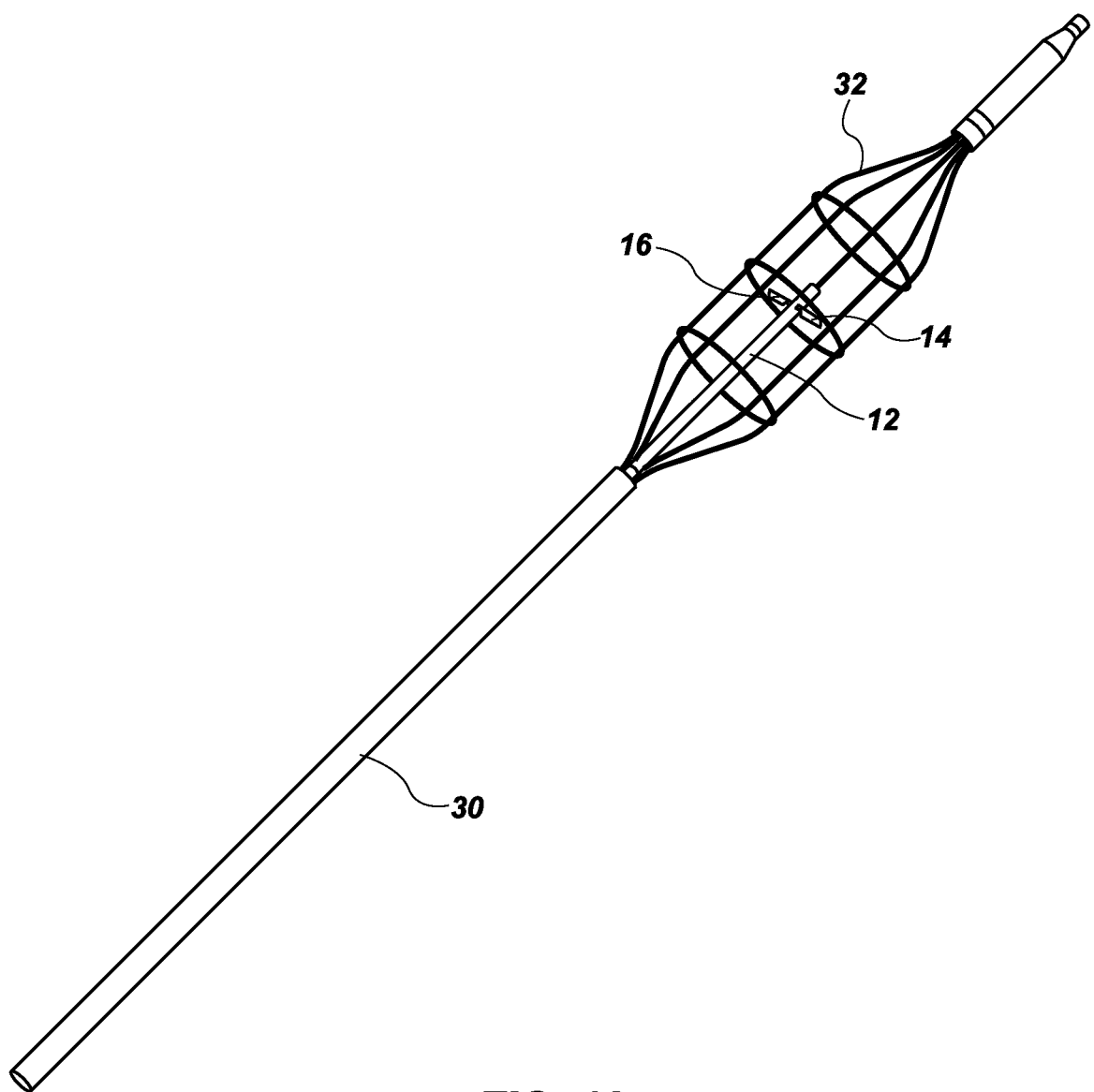
FIG. 16 depicts an alternative embodiment of a stent cage, at the tip of a catheter, which is to surround the rotating impeller blades of the circulatory assist pump.
Figure 17:
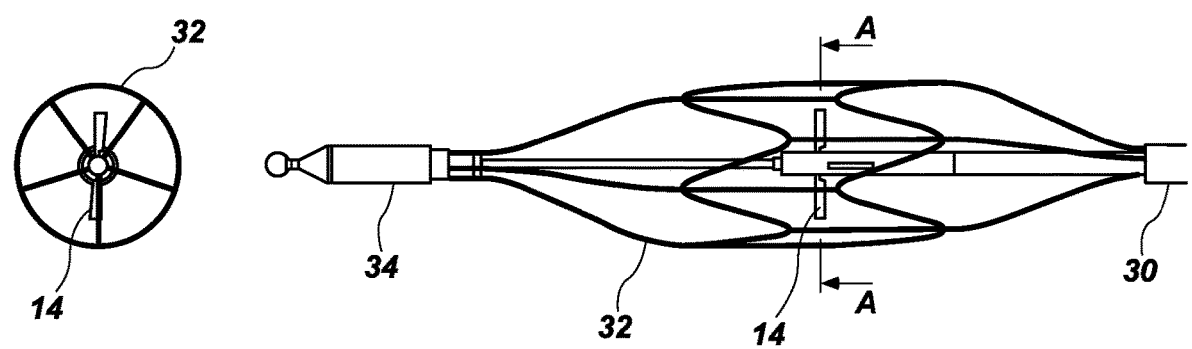
FIG. 17 depicts a catheter with deployed impellers encaged within the stent cage at the tip of the catheter to the right of its associated cross-sectional view taken along lines A-A.

As best depicted in FIG. 15 (a front view of the stent cage), the (aortic) stent cage is preferably designed with a highly open flow to prevent damage to, e.g., the patient's blood cells, such as hemolysis and also reduces the risk of thrombosis.

In certain embodiments (e.g., to reduce the chance that the impeller impacts the stent cage on the side where the PCI catheter is present), the impeller is not extended all of the way (e.g., instead of opening it 11.5 mm wide in a 22 mm aorta, it is only opened, e.g., 8 mm wide, but it still provides 80 to 90% of the flow as compared to when the impeller blades are fully open).

In certain embodiments, the impeller is first started turning with the blades, e.g., only half way open, and after it has been confirmed (e.g., either by measuring flow, viewing the situation, or otherwise) that sufficient gap space exists in the aorta, then the impeller is, e.g., fully opened. This serves to allow one to pump in smaller aortas. A half open impeller diameter is only about 8 mm, while fully open may be, e.g., 11.5 to 18 mm depending on size. Only about 20% of the flow is lost at "half open" in comparison to full open. In some test cases, the flow at "half open" was equal to the flow at full open in animal studies at Tufts Medical Center.

In certain embodiments, magnetized impeller blade tips may be powered wirelessly by an external power belt (electrically powered with a copper coil inside) place around, e.g., the patient's abdomen. Wireless power enables the system to provide the patient with a better quality of life, while reducing the risk of infections and providing the physician with greater patient management options. Wireless power systems are disclosed in, e.g., J. Bowler "This Wireless Heart Pump Battery Could Save Thousands of Lives" *ScienceAlert* (May 26, 2017) and Knecht et al., "High Efficiency Transcutaneous Energy Transfer for Implantable Mechanical Heart Support Systems" (November 2015); DOI: 10.1109/TPEL.2015.2396194, the contents of each of which are incorporated herein by this reference. Such a transcutaneous energy transfer system ("TETS") may be used, e.g., with a ventricular assist device. A TETS system setup includes a power converter, rectifier, and coils. See, also, Ho et al. "Midfield Wireless Powering for Implantable Systems," *Proceedings of the IEEE*, pp. 1-10 (2013 IEEE), the contents of which are also incorporated herein by this reference.

In certain embodiments, WiFi power may be used to control and power the device/system (with WiFi power) instead of using a belt. In such embodiments, repeater, booster, and/or extender technology, may be used with an external wireless power belt to reduce irritation and heating of, e.g., the subject's skin. See, e.g., "WiFi Boosters, Repeaters and Extenders" *RepeaterStore*, (https://www.repeaterstore.com/pages/wifi-booster-repeater-extender-differences) (accessed Feb. 26, 2018), the contents of which are incorporated herein by this reference. The system preferably utilizes wireless repeater power with minimal skin irritation. See, also, D. Gershgorn "Your Wireless Internet Could Power Your Future Devices" *Popular Science*, (https://www.popsci.com/your-wireless-internet-could-power-your-future-devices) (Jun. 3, 2015) and J. Langston "Popular Science names 'Power Over Wi-Fi' one of the year's game-changing technologies," *UW News*, (http://www.washington.edu/news/2015/11/18/popular-science-names-power-over-wi-fi-one-of-the-years-game-changing-technologies/) (Nov. 18, 2015), the contents of each of which are incorporated herein by this reference.

Wireless control of the system can also be used to promote expression of desirable protein(s) via, e.g., implanted micro coils on the stent. See, e.g., US Patent publication US 2017/0266371 A1 to Leonhardt et al. (Sep. 21, 2017), the contents of which are incorporated herein by this reference, for protein expression signals. These micro coils too can utilize wireless energy. Wireless control can extend to pulsatility, speed, and/or impeller angle of the various components of the system. The micro coils can be utilized to control release and/or expression of protein(s) in the aorta, including the release and/or expression of elastin to improve the elasticity of the aorta and mediate stem cell homing and the release and/or expression of follistatin to build new, strong, thick smooth muscle.

The pump may be placed, for example, above the renal arteries in the aorta to aid in kidney function. More flow into the kidneys means more rapid removal of excess fluids, which leads to better revival of kidney function. In certain embodiments, the system preferably uses the full diameter of the aorta to increase pump stability and reduce pump migration.

In animal studies using the described system in sheep and swine, 1.5 to 2.0 liters of true augmented blood (beyond native cardiac output) were provided. With direct flow cannulas placed into the kidneys, the system able to augment renal blood flow by 25 to 50%. The pump was able to generate a gradient of more than 10 mm to unload the left ventricle and achieve improved hemodynamics without any clinically significant steal (reversed flow in the artery). Further, there was a reduced cardiac work index. There was also a significant increase in urine output and no significant hemolysis.

Indications for use of the described system include cardiorenal syndrome, protecting renal function during PCI, and chronic heart failure.

The outwardly foldable impeller uses rotational motion to draw blood in and down from the heart, and moves the blood down the aorta while itself remaining stationary due to the positioning of the cage stent within the aorta. In certain embodiments, controls (e.g., wireless controls) are utilized to modify the rotating impeller blade angles in order to, for example, change flow characteristics. This can be used, e.g., in short durations to dramatically increase flow at the expense of temporary increase of hemolysis, but the system can revert back to a low hemolysis angle shortly thereafter.

The impeller maximizes blood flow, while minimizing hemolysis, power needs, RPMs, and turbulence. The system preferably uses the least RPMs and highest flow and thus lowest hemolysis. The use of a simple impeller lowers the risk of mechanical failure.

Wireless technology can also be used to re-charge a battery or back up a battery for the system as needed.

In one embodiment (not shown), a battery backup power source is housed in the center spindle of the circulatory assist pump, which battery backup power source can be charged either by impeller blade turns or by wireless external recharging.

In certain embodiments, wireless power also powers the turns of the magnetized impeller blades directly, and battery power is only used as a backup.

In certain embodiments, the system includes implanted sensors that assist with a real time, automatic adjustment and management of the circulatory assist support system based upon data provided by the implanted (preferably wireless) sensors. The sensors monitor fluid flow and provide feedback and data to the system, which feedback and data is used to, e.g., adjust the speed and/or angle of the impeller to increase or decrease fluid flow and pressure.

Sensor(s) monitor hemolysis levels and automatically adjust the balance of RPM speed of the impellers and the pulsations of the cuffs (if present), to balance the minimization of hemolysis with the maximization of flow efficiency.

In certain embodiments, the system includes means for synchronous pumping, which is determined by the sensors. See, e.g., Gohean et al. "Preservation Of Native Aortic Valve Flow And Full Hemodynamic Support With The TOR-VAD™ Using A Computational Model Of The Cardiovascular System," *ASAIO J.* 2015 May-June; 61(3): 259-265; doi: 10.1097/MAT.0000000000000190, the contents of which are incorporated herein by this reference.

The range of blood flow parameters in the ascending aorta that can result from various angulations of outflow graft anastomosis of a left ventricular assist device ("LVAD") to the aortic wall, have been quantified as a means to understanding the mechanism of aortic valve insufficiency. See, e.g., Callington et al. "Computational fluid dynamic study of hemodynamic effects on aortic root blood flow of systematically varied left ventricular assist device graft anastomosis design," *J. Thorac Cardiovasc Surg.* 2015 September; 150(3):696-704. doi: 10.1016/j.jtcvs.2015.05.034. Epub 2015 May 15, the contents of which are incorporated herein by this reference.

Thus provided is the automatic adjustment of the impeller speed and pulsations of the pulsating cuff based upon real time pressure differentials and other data from the implanted sensors, which are placed in strategic positions. In a preferred embodiment, the sensors are placed above and below the catheter, cuffs, or stents. Such an embodiment optimizes flow by also timing pulsations of the pulsating cuff and impeller speed/angle with patient conditions and needs, including synchronization thereof with optimal real time pulsatile flow.

With various prior art devices, clinicians need to make manual adjustments of up to a dozen times an hour around the clock to be able to manage circulatory assist support based upon a chosen constant aortic pressure differential range or other sensing parameters. In contrast, the described system can be managed automatically and more frequently with the intention of improving patient outcomes. Furthermore, in designing a wireless power-based system and taking into consideration the risk of mechanical breakdown, demands on the system can be reduced (when patient conditions permit) for a time, allowing the device to "cool off" or "rest." Inversely, the circulatory assist support can be turned up when demands dictate a genuine need and not before.

Such a system permits patient treatment to be customized on a real time personalized basis to provide superior outcomes for patients (e.g., those suffering from cardio-renal dysfunction in the advanced stages of heart failure).

In one embodiment of the system, a first impeller stent pump is positioned in the subject's ascending thoracic aorta, which unloads blood from the subject's heart (e.g., the first impeller stent pump is positioned to withdraw blood from the subject's left ventricle). In such an embodiment, a pulsating, partially ePTFE (expanded polytetrafluoroethylene) covered stent graft with three (3) pulsating bands is preferably positioned in the aorta downstream from the positioned first impeller stent pump. Also, a second impeller stent pump is positioned further downstream in the subject's descending aorta, just above the subject's renal arteries.

Such a three (3) band pulsating aortic stent graft typically a stent made of flexible compliant material (like an intraaortic balloon pump ("IABP") catheter balloon turned inside out). Two of the bands are always firmly against the aorta wall and only one band squeezes inward into the aorta at a time.

Left ventricular unloading is known and described, e.g., in Watanabe et al. "Left Ventricular Unloading Using an Impella CP Improves Coronary Flow and Infarct Zone Perfusion in Ischemic Heart Failure," *J Am Heart Assoc.* 2018; 7:e006462. DOI: 10.1161/JAHA.117.006462, Esposito et al. "Left Ventricular Unloading Before Reperfusion Promotes Functional Recovery After Acute Myocardial Infarction" *Journal of the American College of Cardiology*, Vol. 72, issue 5, pp. 501-514 (Jul. 31, 2018), Saku et al. "Total Mechanical Unloading Minimizes Metabolic Demand of Left Ventricle and Dramatically Reduces Infarct Size in Myocardial Infarction," https://doi.org/10.1371/journal.pone.0152911 (2016), Kapur et al. "Mechanically Unloading the Left Ventricle Before Coronary Reperfusion Reduces Left Ventricular Wall Stress and Myocardial Infarct Size," *Circulation*. 128. 10.1161/CIRCULATIONAHA.112.000029. (June 2013), http://dx.doi.org/10.1161/CIRCULATIONAHA. 112.000029, and "Acute Cardiac Unloading and Recovery," *Interventional Cardiology Review* 2017; 12(2 Suppl 2):1-28. See, also, Esposito M L, Kapur N K. "Acute mechanical circulatory support for cardiogenic shock: the 'door to support' time," *F1000Research*. 2017; 6:737. doi:10.12688/f1000research.11150.1.

The real time auto adjustment technology should serve patients, such as those that have physiologic hemodynamic changes due to things as simple as sleep and exercise with advanced heart failure changes in edema levels and modulation of the pump thrust, volume and impeller speed may serve these patients well. By enabling real time automatic adjustments of circulatory assist pump controls to adjust to the constant turbulent changes in hemodynamic and edema conditions that occur on an ongoing basis in, e.g., advanced heart failure patients.

A preferred aortic stent cage (FIG. 7) is designed to minimize hemolysis, while maximizing flow and stability. It is designed to avoid thick elements and to avoid razor cutting. It maximizes stability and positioning of the system. It presently serves as the best protection against the impeller blade(s) hitting the aortic wall.

The wire diameter of the stent cage circulatory assist catheter should be from about 0.015 to about 0.022 inches; preferably about 0.018 inches. Such a diameter is not too thin to cut blood cells and not too thick to ram them hard damaging them.

The catheter and drive shaft are designed to reduce risk of mechanical breakdown by having fewer bearings, which requires less fluid lubrication and flush. They are also designed to ease placement and minimize FR size. The drive shaft lubrication system preferably has minimal bearings and utilizes liquid cooling and an expanded polytetrafluoroethylene ("ePTFE") liner. ePTFE is commercially available from, e.g., W. L. Gore & Associates.

Preferably, the impeller rotates at a number of revolutions, which is less than 10,000 rpm, preferably on the order of 4,500 rpm. Lower RPMs reduce the risk of mechanical failure and also reduce power needs. This can be important since, as reported by Kormos et al. "Left Ventricular Assist Device Malfunctions: It's More Than Just The Pump," CIRCULATIONAHA.117.027360, originally published Jul. 3, 2017 (doi.org/10.1161/CIRCULATIONAHA.117.027360), 19% of patients suffered battery failure with the Heartmate II over 3 years. Heartmate II (Thoratec Corporation) is a heart pump called a left ventricular assist device (LVAD), which was designed to assist the left side of the heart to pump the blood a body needs. Furthermore, 21% of the HeartMate II patients were reported to have had driveline failure with the HeartMate II. The herein described preferred device having liquid cooled, minimal bearing system with ePTFE line and hydrophilic coated drive shaft act to reduce driveline failures.

Figure 10:
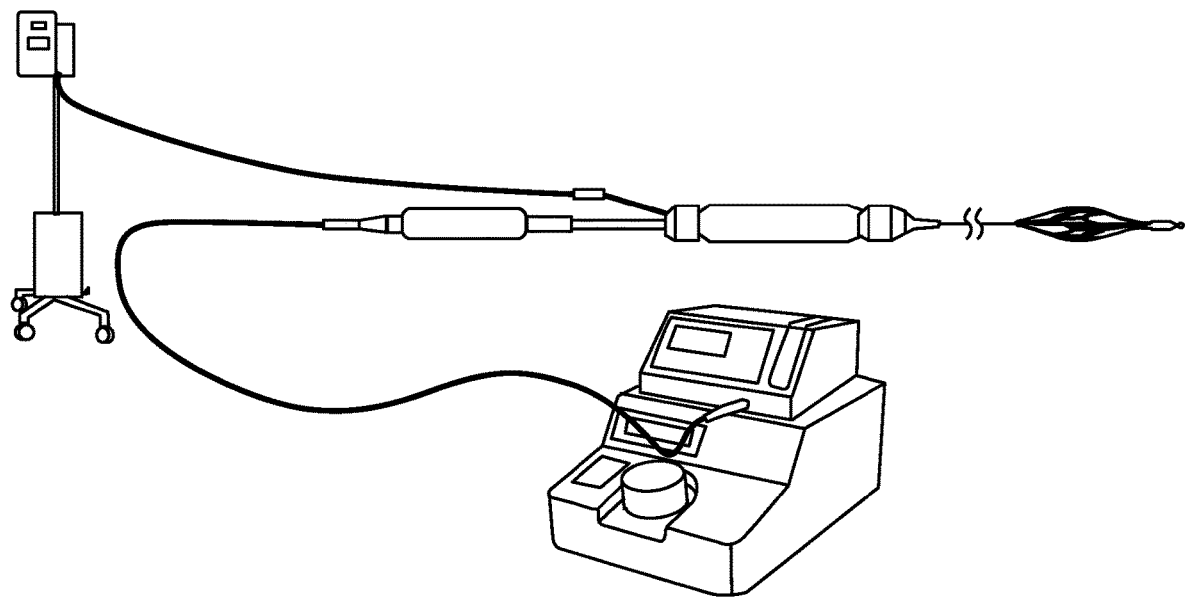
FIG. 10 shows an overall schematic of a system according to the disclosure (not to scale).
Figure 11:
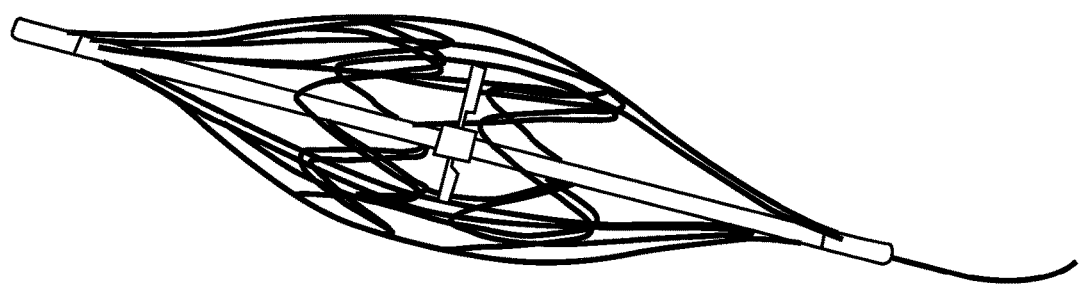
FIG. 11 shows a more detailed view of an alternative embodiment of the device.

As depicted in FIG. 10, the system generally includes a motor and controller, a catheter (e.g., a Biomerics Advanced Catheter from Biomerics, Brooklyn Park, Minn.) that includes the catheter, catheter connector, drive shaft, handle, propeller/impeller, and tip, and a stent cage or frame, e.g., adapted through laser welding for application. As shown in FIG. 14, a "Biomerics Advanced Catheter" has a catheter handle, catheter connector, drive shaft, impeller encaged within the stent cage, and catheter tip.

A preferred handle (FIG. 14) typically has two wheels to manipulate the impeller and deployment of the stent. The first wheel may thus be used to remove the sheath and expose the (closed) impeller pump. The stent typically has a diameter of 20 mm, while the "opened" device typically has a diameter of 22 mm.

A preferred motor is not contained within the patient's circulation (FIG. 10). A preferred controller controls the speed and rpm of the device.

In FIG. 10, the propeller-driven "pump" includes a driveline ("sheath") and the impeller. A proximal sheath is a driveline connecting the pump to a handle (or distal sheath/driveline). The distal driveline connects to a console motor (e.g., depicted is a light and quiet external BLDC motor that is mechanically and thermally isolated and uses a flexible interconnect for ease of positioning, a motor drive control unit and central alarm box). A console extension cable may be used to connect the console to the motor. The console thus may control operation of the pump. An infusion pump (the one depicted in the figure is an off the shelf IVAC/Infusion pump system using standard infusion tubing that terminates in a male Luer connector; medical grade UPS for transport and system power back up) may be used to control the volume of fluid entering the pump (above the distal sheath/driveline). The depicted distal and proximal sheath drivelines use Nitinol inner shafts, a positive action handle for accurate deployment, retraction, and locking of impeller blades. Infusion tubing is then used to deliver fluid as desired.

Such a system can generally involve two different embodiments. First, the temporary circulatory assist support pump(s) is/are placed on the tip of endovascular aortic catheter. Second, the system may include a removable chronic wireless powered implant circulatory assist pump within an aortic stent.

Such a system is designed to reduce heart work load and improve perfusion, improve renal function, normal the hemodynamics of acute decompensating heart failure patients, support heart regeneration procedures, help patients recover from cardiogenic shock, reduce risks associated with percutaneous catheterization interventions ("High Risk PCI"), help patients on the amputation list. Such a system is designed to reduce end diastolic pressure and to reduce end diastolic volume. It is further designed to reduce oxygen demand of myocardium.

Such a system utilizes a relatively straightforward aorta position insertion and is relatively stable over time. It promptly provides hemodynamic support. It is designed to minimize heart valve damage and to minimize coronary re-perfusion injury. It is designed to have low shear stress on blood, and minimize hemolysis.

The wireless power embodiment is designed to reduce infection risk compared to external drive line systems. Also, the wireless power option helps improve the patient's quality of life.

Preferably, the system is utilized with an upper aorta pulsating aortic cuff stent graft (FIG. 8), which improves the total flow of the system, improves hemodynamics, (via the pulsatile flow) improves the release of beneficial proteins for organ health, and reduces RPMs needed by the impeller to reach desired flow rates. A preferred system includes at least three (3) pulsating aortic cuffs on a flexible mesh aortic stent. Pulsating cuffs placed on the top, middle, and bottom of a flexible mesh stent may be controlled via an external abdominal belt.

Figure 12:
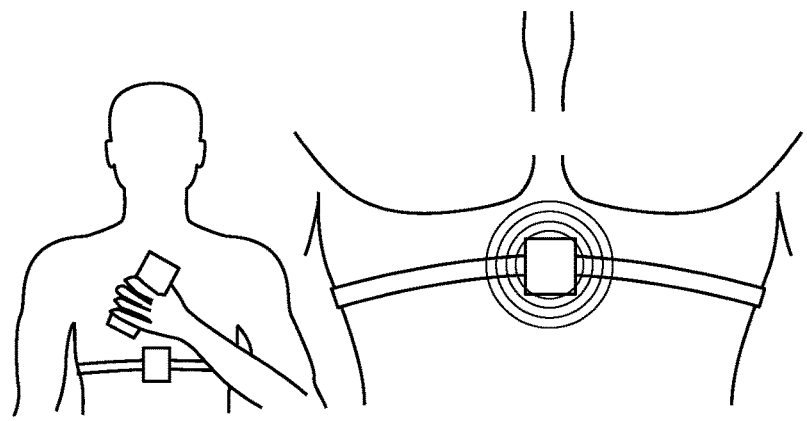
FIG. 12 depicts a belt and controller positioned on a human subject.

Pulsating electromagnetic waves may be, e.g., delivered non-invasively from an abdominal belt (e.g., FIG. 12) in direct communication with the aortic blood flow.

In certain embodiments, the wirelessly driven impeller is contained within a high aortic force protective cage stent (FIG. 7) is placed within such an upper aorta pulsating aortic cuff stent graft in the patient.

The system preferably combines the upper aorta pulsating aortic stent graft with a lower aorta impeller pump within a bare aortic stent to optimize flow with the least power and the least RPMs. Other pulsating aortic stent grafts are on the outside of the aorta, while the described is preferably on the inside. This is more effective, with less variability FIG. 7 shows an embodiment of the device, where a wirelessly driven impeller is contained within a protective aortic cage stent. The depicted device has a cam lobe to release and retract the shaped impeller (e.g., 14.5 mm width) blades, two bearings, and an open protective aortic cage stent. The elements of the protective aortic cage stent are rounded. The depicted device utilizes relatively low RPM speed (7,500 vs. 10,000 to 33,000), maintains arterial pulsatility, and preferably uses the entire aorta of the patient (with the use of a protective aortic cage stent of, e.g., 23.5 mm).

In certain embodiments, the belt, which is to be worn by the patient (see, e.g., FIG. 12), is used to control the pulsatile cuff pulsations, provides wireless power to the lower aortic stent impeller, provides, e.g., vibrational harmonic resonant vibrations or other energy to prevent blood clot formation(s) at, e.g., high risk stagnation points, magnetically or by sound wave pulsations grabs blood and moves it with electromagnetic or sound waves (may reduce 1,500 RPM to reach 4.5 liters flow to 1,000 RPM estimated), and delivers bioelectric signals into tissues and the aorta releasing proteins beneficial to organ and whole body health (note pulsatility also promotes release of beneficial organ health proteins from the aorta and other arteries and tissues).

The removable pulsatile cuff stent may be placed just above the lower impeller aortic stent, which achieves approximately 2 liters per minute flow improvement on its own. The removable pulsatile cuff stent can be designed to push blood up and down or just down by programming the pulsatile elements. The removable pulsatile cuff stent is timed to pulse squeeze in optimization with the heart natural pulsatility. When the pulsatile cuff stent is in place pulsating, the impeller RPM may be reduced to 1,500 RPM to reach 4.5 liters per minute flow (estimated). This cuff placement provides the option for pulsatile flow circulatory assist augmentation.

Pulsatile stent grafts (see, e.g., FIG. 8) are disclosed in, e.g., Palma et al. "Pulsatile stent graft: a new alternative in chronic ventricular assistance," *Revista Brasileira de Cirurgia Cardiovascular* (2013), 28(2):217; http://dx.doi.org/10.5935/1678-9741.20130031, the contents of each of which are incorporated herein by this reference.

In one embodiment, a pulsatile stent graft may be included within the system, placed mid-aorta, while substantially continuous impeller power is applied in the bare aortic stent in the lower aorta.

Preferred such systems for use herein are described in: Pahlevan and Gharib "A wave dynamics criterion for optimization of mammalian cardiovascular system," *J. Biomech.* 2014 May 7; 47(7):1727-32. doi: 10.1016/j.jbiomech.2014.02.014. Epub 2014 Feb. 20., Pahlevan and Gharib "A Bio-Inspired Approach for the Reduction of Left Ventricular Workload," *PLOSone*, (Jan. 24, 2014); https://doi.org/10.1371/journal.pone.0087122, Pahlevan and Gharib "Aortic Wave Dynamics and Its Influence on Left Ventricular Workload," *PLOSone*, (Aug. 11, 2011); https://doi.org/10.1371/journal.pone.0023106, U.S. Pat. No. 9,125,655 to Gharib et al. (Sep. 8, 2015) for Correction and Optimization of Wave Reflection in Blood Vessels; U.S. Pat. No. 7,998,190 to Gharib et al. (Aug. 16, 2011) for Intravascular Miniature Stent Pump; U.S. Pat. No. 7,163,385 to Gharib et al. (Jan. 16, 2007) for Hydroimpedance Pump; U.S. Pat. No. 8,092,365 to Rinderknecht et al. (Jan. 10, 2012) for Resonant Multilayer Impedance Pump; U.S. Pat. No. 7,883,325 to Kheradvar et al. (Feb. 8, 2011) for Helically Actuated Positive-Displacement Pump and Method and U.S. Pat. No. 9,125,655 B2 to Phalevan, the contents of each of which are incorporated herein by this reference.

Preferably, the pulsating cuff pump is positioned in the upper aorta of the subject above the stent cage impeller, which is positioned lower in the aorta. Preferably, two aortic stents in series in the aorta, the top aortic stent being fully pulsatile and the bottom aortic stent semi-pulsatile (meaning it turns, but it turns so far away from heart that it does not take away pulsaltility, it just accelerates it). This relative positioning of the two pumps maximizes flow while minimizing impeller RPM. The combination of the pulsating cuff aortic stent graft in the upper aorta with the impeller pump/aortic stent in the lower aorta reduces RPMs from, e.g., 4,500 rpm to attain 4.5 liters per minute flow to 1,500 rpm, and provides advantages in terms of hemodynamics, expression of protein(s), and flow not found in either device alone. Less RPMs requires less power, which translates to a system that is easier to power wirelessly. There is also less of a risk of a mechanical breakdown, and less resulting damage to blood cells from hemolysis.

Such a system, may be combined with, e.g., a vibrating harmonic resonant device to reduce and hopefully prevent blood clots, which is "the Achilles' heel" of chronic implants. A harmonic resonant vibration system to reduce blood clots in such a system is described in U.S. Provisional Patent Application No. 62/577,395, filed Oct. 26, 2017, to Leonhardt et al. for "Harmonic Vibration Device to Prevent Blood Clot, Calcification and/or Plaque Formation on Blood Contact Surfaces," the contents of which are incorporated herein by this reference. The system may also (or alternatively) utilize an electric charge surface treatment of the implant to further reduce risk of blood clots, calcification, and plaque forming on the device.

In certain embodiments, the system includes a bi-layer magnetic fluid graft that further increases flow without hemolysis (e.g., the system utilizes a magnetic fluid-filled silicon (bi-layer) graft liner placed on the inside of the impeller stent) where the pulsaging wave augment aortic flow).

In certain embodiments, the system magnetically "grabs" blood via iron particles in blood and manages flow wave pulses to optimization and flow optimization timing, which further enhances flow without increasing hemolysis. For example, pulsed electromagnetic waves cam be utilized to "grab" the iron in the patient's blood and move it in waves via an external belt.

The system can further include bioelectric coils on the stent to control expression and/or release of protein(s) such as those that build strength of aortic muscle and/or aid in kidney recovery. See, e.g., the earlier incorporated US Patent publication US 2017/0266371 A1 to Leonhardt et al. (Sep. 21, 2017) and/or Macfelda et al. "Bioelectrical signals improve cardiac function and modify gene expression of extracellular matrix components" *ESC Heart Failure* 2017; 4: 291-300 (published online 30 Jun. 2017); DOI: 10.1002/ehf2.12169, the contents of which are incorporated herein by this reference. Via the system, inflammation and blood pressure can be managed with bioelectric signal protein expressions and membrane potential management. The platform can also be used to aid in the creation and control of smooth muscle formation in the aorta.

In certain embodiments, wireless powered and programmed micro coils are utilized with the system to control aortic tissue protein expressions and to increase smooth muscle mass and to control pulsations of natural aortic muscle, a cellular muscle-based "second heart." For example, pacing the timed electrical pulse signals may be utilized to trigger contractions of smooth muscle so to make the natural aorta a beating "second heart" optimized with native pulsatile flow.

The wireless powered and programmed micro coils can be further used to control chronic inflammation and blood pressure with real time reads and adjustments.

The system itself preferably utilizes programmed, real-time optimization to manage flow, hemolysis, power, and patient hemodynamics real time. The programming can be configured to change parameters, e.g., with the subject's exercise, sleep, heart failure conditions, etc., including monitoring fluid level in the patient's lungs, etc.

In certain embodiments, the system includes vibrational harmonic resonant tuned technology, which reduces risk of thrombosis (blood clot formations), reduces risk of plaque or calcification formations, increases gas exchanges in aorta, and promotes healthy protein release in aorta. It is relatively easily mounted into the same belt providing wireless power and controlling pulsating implants and micro coils. Including micro coils controls protein expression in the aorta to, e.g., increase elasticity, control blood pressure, improve organ health, and control inflammation Blood clots have been the "Achilles heel" of many other chronic implant devices. Resonant harmonic vibrational energy technology may be utilized to reduce the risk of this problem. Tuned harmonic resonant vibration may be used to prevent blood clot formation at high risk stagnation points on the device. The harmonic resonance for each high risk stagnation point may be individually customized and stored in a microprocessor. The vibrational energy may be delivered in pulses in a loop hitting each high risk location of the device to prevent a large accumulation of a blood clot, which might develop.

Pulsatility results in healthier hemodynamics, less risk of thrombosis, together with cellular arterial wall protein expression for superior organ recovery and patient well-being. The device described herein combines the best of pulsatile flow with continuous flow. Using pulsatile and continuous flow optimizes hemodynamics and lessens the risk of thrombosis.

In certain embodiments, the system utilizes a motor console for precision performance and low vibration, with flushing built in.

In certain embodiments, BION micro coil implants are incorporated into the system. They may be utilized to release proteins for the heart, aorta, arteries, lungs and kidney health. They also be utilized to provide real time data on performance, flow, pressures etc.

The system can be utilized variously. For instance, as a temporary catheter alone for 6 to 72 hours. As a temporary catheter with removable pulsating cuff stent in series with both removed after use of 6 to 72 hours. The temporary use catheter may be removed, but the pulsating cuff stent may be left in place for chronic long term use. The catheter and drive shaft can be disconnected from the impeller stent, which can then be switched to wireless power on a standalone basis.

In certain embodiments, there are two aortic stent based circulatory assist pumps in series in the aorta, one upper and one lower, the upper one being pulsatile.

In certain embodiments, the impeller stent can be left out/removed, and the pulsating aortic cuff stent left in place.

The device may be removed should the need for the device abate (e.g., upon recovery of the patient). For removing the device, a modified Seldinger technique (or comparable technique) can be applied in reverse utilizing a catheter that interacts with, e.g., the pump for removal. The impeller blades may first be retracted and the stent cage then collapsed about it to reduce the cross-sectional diameter of the pump to aid in removal.

The foregoing can be supported with a vibrational harmonic resonance technology for preventing blood clot formations (thrombosis), but this is especially preferred when the system is used for chronic implant use. Furthermore, the foregoing can be supported with the release of bioelectrically controlled release of protein(s) from, e.g., the aorta, tissues, and arteries to assist in healing. Further, the foregoing can be supported by electromagnetic wave or sound wave pulsations to further enhance blood flow improvement.

Although it is an advantage of the device to not need to cross the aortic valve, in certain embodiments, the described encaged pump system may be combined advantageously with a device that does cross the aortic valve (e.g., in high head/low flow applications). Such a system includes placement of the device that does cross the aortic valve at the tip of the catheter, beyond the aortic valve and placement of the herein described second device encaged impeller (bare aortic stent and pump on the catheter) proximal the renal arteries that feed the kidneys. The first such pump may be a second of the herein described pumps or a pump akin to the HeartMate PHP percutaneous heart pump. The second such pump may be that of FIG. 11 adapted by extending the drive shaft further to interact and drive the first pump. The two pumps are placed on the same catheter and may utilize the same drive shaft. The first pump operating high near the heart (for left ventricle unloading) past the heart valve and the second pump in positioned in the lower aorta, just above the renal arteries (for renal output improvement), i.e., the second pump in the mid to lower stomach and the first pump up in the upper mid chest (usually 20 to 30 cm in most people).

In such a situation, sometimes the required operating conditions for a patient are beyond the reach of a single, standard pump, and it is best to combine simple pump performances that add up to the necessary requirements. Positioning pumps in series as described herein, or connected along a single line, allows the system to add the head from each pump together to meet the high head, low flow system requirements. This is because the fluid pressure increases as the continuous flow passes through each pump, much like how a multi-stage pump works. For example, if two of the same pumps are in series, the combined performance curve will have double the head of a single pump for a given flow rate. For two different pumps, the head is still added together on the combined pump curve, but the curve will most likely have a piecewise discontinuity.

In situations where a high, constant pressure is required, speed control may need to be included with, for example, the first pump in such a system. This configuration achieves the high pressure that is needed, while keeping a low flow, because the fixed-speed pump feeds into the speed-controlled pump, which adjusts its output with a pressure transmitter to add only enough head to maintain a constant pressure. This device would combine the benefits of both designs in one product. Having two in series reduces RPMs needed for both to get same flow improvement.

The disclosure is further described with the aid of the following Example.

EXAMPLE I

A prior art IMPELLA 2.5® heart pump (Abiomed) pulls blood from the left ventricle through an inlet area near the tip and expels blood from the catheter into the ascending aorta. The IMPELLA 2.5® heart pump is designed to temporarily (≤6 hours) protect the patient hemodynamically during a high-risk procedure (e.g., in patients experiencing: advanced heart failure, cardiogenic shock, and/or post-cardiotomy cardiogenic shock). The IMPELLA 2.5® device is inserted into a patient via a standard catheterization procedure through the femoral artery, into the ascending aorta, across the valve and into the left ventricle. The IMPELLA 2.5® device is thought to stabilize hemodynamics, unloads the left ventricle, perfuses the end organs, and allows for recovery of the native heart.

The IMPELLA 2.5® device spins at approximately 50,000 RPM with flows of 2.5 l/min on the highest possible setting. Reportedly, Abiomed's 5.0 device spins at 33,000 RPM with maximum flows of 5.3 l/min on the highest possible setting.

The IMPELLA 2.5® device needs 55,000 RPMs (turns of impeller) to achieve 4.5 liters per minute flow at the level of the renal arteries for cardio-renal dysfunction recovery.

Utilizing the device of FIG. 7, 4.5 liters flow at the level of the renal arteries (goal is to increase renal output and recovery) were achieved in a pig with only 4500 RPMs. Lower RPMs results in less damage to blood cells (hemolysis), less heat, less wear, less risk of mechanical breakdown, and less power needs.

The device of FIG. 7 is wireless powered when combined with a second pulsating cuff stent higher in the aorta achieves 4.5 liters flow with only 1,500 RPMs, and may be left in the patient up to 5 years. The IMPELLA 2.5® device is to be removed in 72 hours and is connected by a drive shaft to an external motor.

Figure 9:
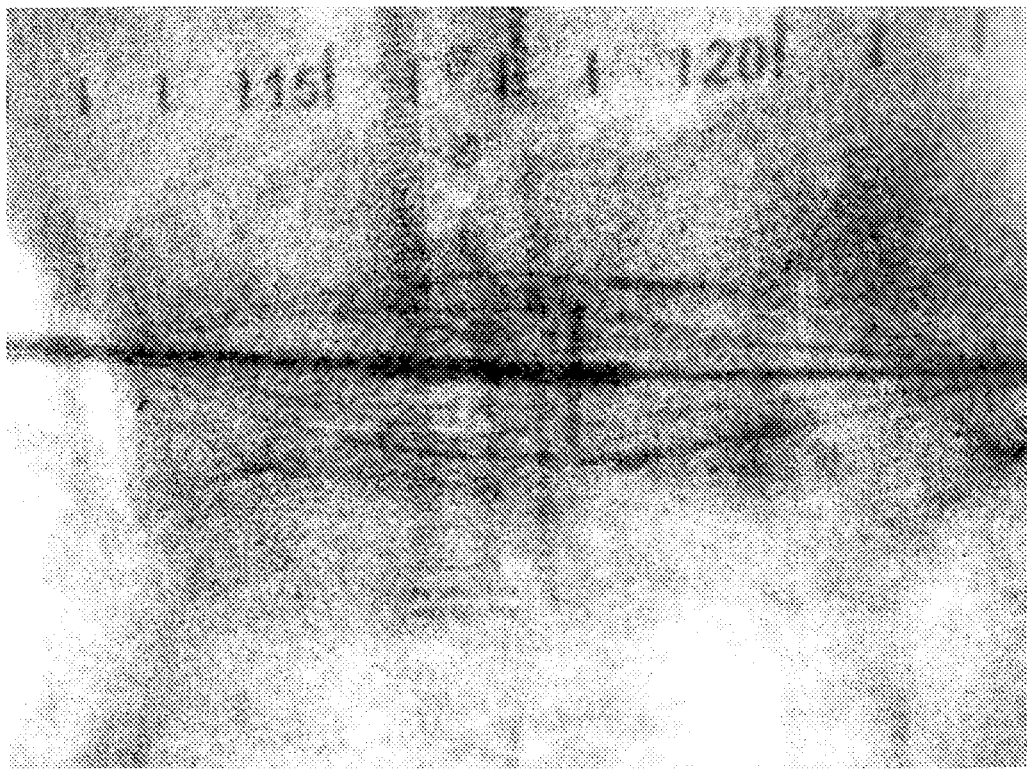
FIG. 9 is a picture of a device as described herein connected to a drive axis placed within a pig.

FIG. 9 is a picture of a device comprising the impeller and surrounding stent cage implanted and actuated within a pig cadaver.

The IMPELLA 2.5® device needs to spin its impellers at 18,500 to 50,000 RPM to reach 4.5 liters per minute flow through the device, which increases risk of hemolysis and mechanical breakdown. The IMPELLA 2.5® device does not reach 4.5 liters per minute true flow in the patients with these RPMs, only these flow rates through the small orifices of the associated small diameter catheters. The actual patient flow improvement is less than ½ this device flow rate, i.e., under 2.25 liters per minute patient flow improvement.

In certain embodiments, the device utilizes strong radial force deployment to maintain its position in the aorta and occupies nearly all (or all) of the entire inner diameter of the subject's aorta, and thus the 4.5 liters per minute flow through device is also 4.5 liters per minute flow improvement for the patient. The strong radial force utilized in the system limits repositioning of the device. Occupying this much of the aorta allows for the use of the relatively lower rpm of the device.

Wireless power, which powers the device of FIG. 7, results in a higher quality of life for patients. The patient can go home, with less risk of infection and less risk of movement of position.

EXAMPLE II

The herein described circulatory assist device is combined with a heart regeneration bioelectric stimulator, micro infusion pump, and mixed composition for implantation into a subject's aorta as described herein. In such a combination, the circulatory assist pump off loads work load from the heart, thus improving perfusion to improve regeneration results. The subject's heart recovers over time.

Expression of desirable protein(s) may be accomplished via, e.g., implanted micro coils on the stent. See, e.g., the earlier incorporated US Patent publication US 2017/0266371 A1 to Leonhardt et al. (Sep. 21, 2017) and/or the earlier incorporated Macfelda et al. "Bioelectrical signals improve cardiac function and modify gene expression of extracellular matrix components" *ESC Heart Failure* 2017; 4: 291-300 (published online 30 Jun. 2017).

As previously described, such micro coils too can utilize wireless energy. Wireless control extends to pulsatility, speed, and/or impeller angle of the various components of the system.

EXAMPLE III

Figure 13:
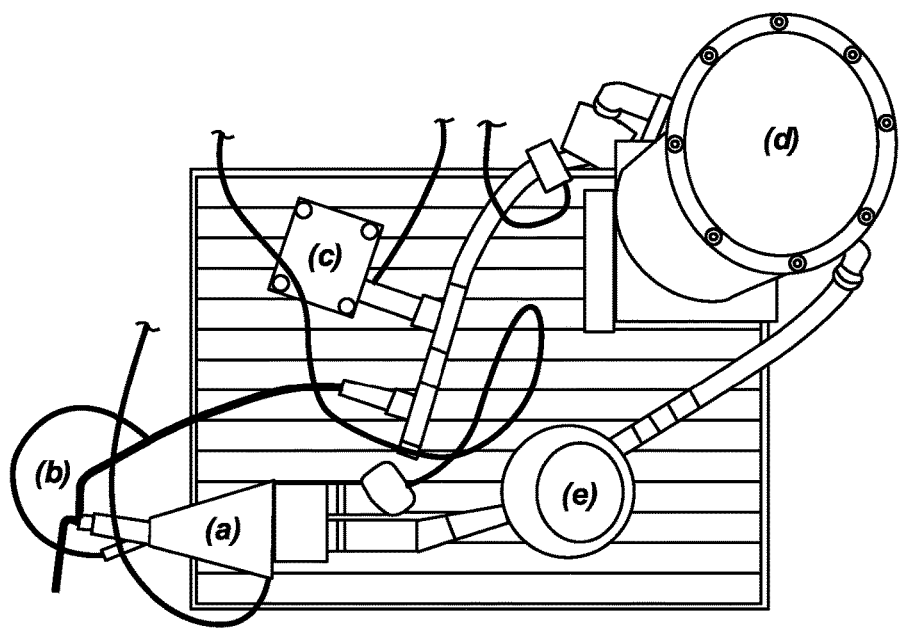
FIG. 13 depicts a physiologically accurate mock circulation loop.

As depicted in FIG. 13, a physiologically accurate mock circulation loop (static mock flow loop) is used to test the devices at the Cardiovascular Innovation Institute in Louisville, Ky. FIG. 13 shows the dynamic mock flow loop includes (a) a left ventricle, (b) a left ventricular assist device (LVAD), (c) systemic compliance, (d) venous reservoir, and (e) atrial elements. These mock flow loops quantify the hydraulic and hemodynamic performance of the LVAD.

EXAMPLE IV

A circulatory assist pump 10 (FIGS. 16 & 18) is made and encaged within a stent cage 32 (FIGS. 17 & 18) placed near the catheter's tip 34. The impeller blades 14, 16 are 14.5 mm long from tip to tip and are made of 17-4PH stainless steel.

The encaged circulatory assist pump (FIG. 18) is placed in the subject's aorta just above the renal arteries. The stent cage is expanded and the impeller blades extended within the aorta.

The impeller blades are set to rotate at 7,500 rpm in a 20 mm aorta distended with stent radial force to 22 mm, thus producing an increase of 1.5 liters per minute flow from a starting base of 3.5 liters per minute increasing to 5.0 liters per minute total flow in the aorta just above the renal arteries. Dependent on, for example, the patient being treated, an optimal pump speed can be as high as 10,000 rpm.

Computational fluid dynamics testing is conducted used to determine flow rates (particularly flow into the renal arteries), aortic pressure differential, and coronary flow rates, and thus brain and hemolysis risk.

EXAMPLE V

A circulatory assist pump is made and encaged within a stent cage. The impeller blades have an impeller diameter of 13.5 mm long from tip to tip and are made of 17-4PH stainless steel.

The impeller blades are set to rotate at 7,500 rpm in an open stent (outer diameter) aorta distended of 22.86 mm.

The boundary conditions are as follows:
Flow Inlet (L/min) of 3.5, 4.5, and 5.5.
Impeller speeds (rpm) of 7,500, 10,500, and 15,000.

EXAMPLE VI

An upper aortic pulsating stent graft useful herein has the following dimensions and specifications:
Outer Diameter of 24 mm aortic stent for being placed, e.g., in a 20-22 mm aorta
Total Length of 6 cm before placement in the 22 mm aorta (lengthens when compressed).
Hoop Strength of 15.8 N/cm
Radial Resistance Force of 1.27 N/cm
Chronic Outward Force of 0.31 N/cm
Three (3) pulsating wireless powered bands each 1.5 cm wide each wrapped around stent. Only one pulsates at any given time.
Aortic stent is ¾'s covered in ePTFE (expanded polytetrafluoroethylene) matching with positions of pulsatile bands.
Each pulse band on each pulsation moves covered stent inward into the aorta 3 mm (a 3 mm aortic pulse wave).
Pulsation is time matched to natural pulses of the subject's heart (e.g., "native flow") with a slight time delay for time for pulsed blood flow to reach the aorta.

EXAMPLE VII

Powering an impeller pump positioned within a stent cage of FIG. 7 was successfully demonstrated by the Queensland University of Technology (QUT) in Brisbane, Australia, using the QUT wireless power system. An AC/DC power supply providing 1.6 volts connected to a transmitter coil to a series capacitor coil and inverter (set at 1 megahertz) and controller. The system was about 1.3 Watt.

What is claimed is:

1. A system for a circulatory assist pump, which system maintains arterial pulsatility, the system comprising:
    a circulatory assist pump, comprising:
        a distal tip; and
        a proximal end opposite the distal tip, the proximal end removably connectable to a catheter; and
        an impeller system between and connected to the distal tip and the proximal end, the impeller system including pivotally mounted arm-like impeller blades, which are foldable and retractable, which arm-like impeller blades, during operation rotate to draw blood down a subject's aorta from the subject's heart; and
    a stent cage encaging the circulatory assist pump, the stent cage comprising wire-like elements having ends secured to the distal tip and the proximal end of the circulatory assist pump, wherein the stent cage expands and compresses and is of a size and shape to allow a highly open flow of blood therethrough when placed within the subject's aorta, and further having an expanded circumference sized to be stable against the subject's aortic wall wherein the wire-like elements of the stent cage distend the subject's aortic wall to positionally affix the stent cage to the subject's aorta during operation of the impeller system while allowing the subject's aorta to maintain its natural pulsatility;
    wherein, when the system is positioned and operated in the aorta proximal and above the renal arteries of the subject, natural aortic wall pulsatility is maintained.

2. A method of treating a subject suffering from heart disease, the method comprising:
    implanting the system of claim 1 into the subject and utilizing the impeller system of arm-like impeller blades to draw blood down the aorta from the subject's heart.

3. The method according to claim 2, wherein the system is controllable wirelessly.

4. The method according to claim 3, wherein the wireless control controls pulsatility, speed, and/or impeller angle of the system.

5. The method according to claim 2, wherein, after implantation, the impeller rotates at less than 10,000 RPM.

6. The method according to claim 5, wherein, in operation, the impeller rotates on the order of 4,500 RPM to achieve 4.5 liters flow at the level of the subject's renal arteries.

7. The method according to claim 2, wherein the impeller system is powered wirelessly.

8. A method of treating a subject suffering from heart disease, the method comprising:
    utilizing the system of claim 1 to treat the subject.

9. The method according to claim 8, further comprising:
    implanting at least one sensor into the subject.

10. The method according to claim 9, wherein the sensor(s) monitor(s) fluid flow in the aorta and provides feedback and data to the system, and wherein the feedback and data are used to adjust the speed and/or angle of the arm-like impeller blades in the subject's aorta and/or to increase or decrease fluid flow and pressure in the subject's aorta.

11. The method according to claim 8, further comprising:
    promoting protein expression and or release within the subject's aorta.

12. The method according to claim 8, further comprising:
    utilizing vibrating harmonic resonance to reduce blood clots in the subject.

13. The system of claim 1, wherein the system is controllable wirelessly.

14. The system of claim 13, wherein the wireless control controls pulsatility, speed, and/or impeller angle of the system.

15. The system of claim 13, further comprising:
    an external belt, for placement about the subject, for controlling and/or powering the system.

16. The system of claim 1, further comprising a drive shaft for the impeller system.

17. The system of claim 16, wherein the impeller system has an ePTFE liner.

18. The system of claim 1, wherein the circulatory assist pump comprises a cam that extends and withdraws the arm-like impeller blades into and out of a catheter associated with the cam.

19. The system of claim 1, further comprising a pulsating cuff for placement upstream the stent cage in the aorta.

20. The system of claim 1, wherein the impeller system is powered wirelessly.

* * * * *